(12) United States Patent
Teles et al.

(10) Patent No.: US 9,775,814 B2
(45) Date of Patent: Oct. 3, 2017

(54) ENTERIC SOFT CAPSULE COMPOSITIONS

(71) Applicant: PATHEON SOFTGELS INC, High Point, NC (US)

(72) Inventors: Helena Maria de Albuquerque Ferreira Teles, Breda (NL); Henricus Marinus Gerardus Maria van Duijnhoven, den Bosch (NL); Mélanie Françoise Géraldine Bayarri, Tilburg (NL)

(73) Assignee: PATHEON SOFTGELS INC., High Point, NC (US)

( * ) Notice: Subject to any disclaimer, the term of this patent is extended or adjusted under 35 U.S.C. 154(b) by 0 days.

(21) Appl. No.: 14/744,057

(22) Filed: Jun. 19, 2015

(65) Prior Publication Data

US 2015/0366815 A1    Dec. 24, 2015

Related U.S. Application Data

(60) Provisional application No. 62/015,063, filed on Jun. 20, 2014.

(51) Int. Cl.
  *A61K 9/48*   (2006.01)
  *A61K 9/40*   (2006.01)

(52) U.S. Cl.
  CPC ............ *A61K 9/4866* (2013.01); *A61K 9/485* (2013.01); *A61K 9/4808* (2013.01); *A61K 9/4825* (2013.01); *A61K 9/4833* (2013.01); *A61K 9/4858* (2013.01)

(58) Field of Classification Search
  None
  See application file for complete search history.

(56) References Cited

U.S. PATENT DOCUMENTS

| | | | |
|---|---|---|---|
| 3,826,666 A | 7/1974 | Hirai et al. | |
| 3,959,540 A | 5/1976 | Leiberich et al. | |
| 4,138,013 A | 2/1979 | Okajima | |
| 4,500,453 A | 2/1985 | Shank | |
| 4,790,881 A | 12/1988 | Wittwer et al. | |
| 4,816,259 A | 3/1989 | Matthews et al. | |
| 5,146,730 A | 9/1992 | Sadek et al. | |
| 5,194,464 A | 3/1993 | Itoh et al. | |
| 5,459,983 A | 10/1995 | Sadek et al. | |
| 6,193,999 B1 | 2/2001 | Gennadios | |
| 6,331,316 B1 | 12/2001 | Ullah et al. | |
| 6,482,516 B1 | 11/2002 | Sadek et al. | |
| 8,685,445 B2 | 4/2014 | Hassan et al. | |
| 2001/0051188 A1 | 12/2001 | Ullah et al. | |
| 2005/0095285 A1 | 5/2005 | Rao et al. | |
| 2006/0115527 A1 | 6/2006 | Hassan et al. | |
| 2006/0165778 A1 | 7/2006 | Hassan et al. | |
| 2007/0082046 A1* | 4/2007 | Chidambaram | A61K 9/4816 424/456 |
| 2007/0098786 A1* | 5/2007 | Chidambaram | A61K 9/4816 424/456 |
| 2007/0196463 A1 | 8/2007 | Podili et al. | |
| 2012/0301546 A1* | 11/2012 | Hassan | A61K 31/00 424/465 |
| 2013/0034605 A1* | 2/2013 | Kshirsagar | A61K 9/2886 424/472 |
| 2014/0348879 A1 | 11/2014 | Hassan et al. | |

FOREIGN PATENT DOCUMENTS

| | | |
|---|---|---|
| DE | 3222476 A1 | 12/1983 |
| EP | 0092908 A2 | 3/1983 |
| EP | 1184033 A1 | 3/2002 |
| WO | 9850019 A1 | 11/1998 |
| WO | 0067723 A2 | 11/2000 |
| WO | 0124780 A2 | 4/2001 |
| WO | WO 02/49637 A1 | 6/2002 |
| WO | 2004012701 A2 | 2/2004 |
| WO | 2004030658 A1 | 4/2004 |

OTHER PUBLICATIONS

Eudragit NE 30D—[retrieved from on-line website: http://eudragit.evonik.com/product/eudragit/en/products-services/eudragit-products/sustained-release-formulations/ne-30-d/pages/default.aspx, last visit Mar. 31, 2016]).*
Eudragit L 100—[retrieved from on-line website: http://eudragit.evonik.com/product/eudragit/en/products-services/eudragit-products/enteric-formulations/l-100/Pages/default.aspx, last visit Mar. 31, 2016].*
Eudragit FS 30D—[retrieved from on-line website: http://eudragit.evonik.com/product/eudragit/en/products-services/eudragit-products/enteric-formulations/fs-30-d/pages/default.aspx, last visit Mar. 31, 2016].*
Waybackmachine (Eudragit NE 30D—[retrieved from on-line website: https://web.archive.org/web/*/http://eudragit.evonik.com/product/eudragit/en/products-services/eudragit-products/sustained-release-formulations/ne-30-d/pages/default.aspx, last visit Mar. 31, 2016]).*
Waybackmachine (Eudragit L100: [retrieved from on-line website: https://web.archive.org/web/20160328193204/http://eudragit.evonik.com/product/eudragit/en/products-services/eudragit-products/enteric-formulations/l-100/pages/default.aspx, last visit Mar. 31, 2016]).*
Waybackmachine (Eudragit FS 3D; [retrieved from on-line website: https://web.archive.org/web/*/http://eudragit.evonik.com/product/eudragit/en/products-services/eudragit-products/enteric-formulations/fs-30-d/pages/default.aspx, last visit Mar. 31, 2016]).*
Nikam et al., "Eudragit a versatile polymer: a review", Pharmacologyonline 1:152-164 (2011, pp. 152-164).*
International Search Report for PCT/US2015/036539, mailed Sep. 25, 2015.
Zu, Y., et al., "Effect of neutralization of poly(methacrylic acid-co-ethyl acrylate) on drug release from enteric-coated pellets upon accelerated storage", Drug Development and Industrial Pharmacy, vol. 33 (2007), pp. 457-473.

* cited by examiner

*Primary Examiner* — Ernst V Arnold
*Assistant Examiner* — Kyung Sook Chang
(74) *Attorney, Agent, or Firm* — Brinks Gilson & Lione

(57) ABSTRACT

Described herein are enteric soft capsules comprising gastric resistant polymers and gelatin and methods for manufacturing the same. The enteric soft capsules described herein have enhanced enteric and elastic properties and are simpler to manufacture and produce.

22 Claims, No Drawings

ENTERIC SOFT CAPSULE COMPOSITIONS

CROSS REFERENCE TO RELATED APPLICATIONS

This application claims priority to U.S. Provisional Patent Application No. 62/015,063, filed Jun. 20, 2014, which is incorporated by reference herein in its entirety. This application is related to International Patent Application No. PCT/US2015/36539, filed on Jun. 19, 2015, which is incorporated by reference herein in its entirety.

TECHNICAL FIELD

Described herein are enteric soft capsules comprising gastric resistant polymers and gelatin and methods for manufacturing the same.

BACKGROUND

The use and manufacture of enteric dosage forms are known in the art. Such dosage forms are described in Remington's Pharmaceutical Sciences, 18$^{th}$ ed., Mack Publishing Co., Easton, Pa. (1990). Enteric dosage forms are useful for protecting the contents of the dosage form from the gastric conditions of the stomach and/or to protect gastric tissue from an irritant material contained in the dosage form. A further use for enteric dosages is prevention of a lasting, unacceptable mouth odor resulting from ingestion of substances like garlic or fish oil. Enteric dosage forms are also used to provide slow, controlled, or delayed release of a substance.

Enteric-coated dosage forms are typically produced by a film coating process, where a thin film layer of an acid-insoluble (enteric) polymer is applied to the surface of a pre-manufactured dosage form, such as a tablet, and to a lesser extent hard and soft capsules. The enteric coating method involves spraying an aqueous or organic solution or suspension of one or more enteric polymers onto tumbling or moving tablets or capsules, followed by drying at elevated temperatures.

Enteric soft capsules are described in U.S. Pat. No. 8,685,445, where an acid-insoluble polymer is combined with a water soluble film forming polymer in the presence of an alkaline aqueous solvent. This formulation resulted in acid resistant capsule shells where the enteric polymer was integrated into the capsule shell. This approach eliminated problems associated with enteric coatings, such as the presence of "orange peel" surface formation, also known as surface roughness, mottling, or lack of surface homogeneity. In addition, the integrated acid-insoluble polymers prevented enteric coat integrity failures, such as in the cases of cracking or flaking of the coating.

However, these enteric polymer formulations can result in gel masses prior to capsulation that are often brittle and viscous, which can reduce the efficiency of the overall manufacturing process (e.g., through the formation of twin capsules). These aspects necessitate the use of additional plasticizers or other softening agents. Furthermore, these integrated enteric polymers required the use of volatile alkaline agents, which require additional safety measures to be in place during manufacturing.

Described herein are gastric resistant capsule shells with integrated enteric polymers, which can encapsulate liquid, semi-solid, or solid matrix fills that contains a gastric resistant polymer or polymers at relatively low concentrations, which obviate the aforementioned limitations. In addition, these enteric soft capsules present unexpectedly enhanced enteric properties and require the use of less plasticizing agents. The gel mass is simpler and safer to manufacture because the use of volatile alkali agents is not required. Furthermore, the enteric soft capsules described herein have an increased compatibility with alkali-labile active drug substances.

SUMMARY

One embodiment described herein is an oral enteric soft capsule shell formed from a gel mass composition comprising: (a) at least one or more film-forming polymers; (b) at least one or more acid-insoluble polymers; (c) at least one or more plasticizers; (d) a solvent; and (e) optionally, an alkali neutralizing agent. In one aspect described herein, the one or more film-forming polymers comprises about 10% to about 40% of the total gel mass. In another aspect described herein, the one or more film-forming polymers comprises gelatin, hydroxypropylmethylcellulose (HPMC), or carrageenan. In one aspect described herein, the one or more film-forming polymers comprises Type A gelatin or Type B gelatin. In another aspect described herein, the Type A gelatin comprises acid bone, pig skin, poultry, fish, gelatin hydrolysate, or acid hide; and the Type B gelatin comprises lime bone gelatin. In another aspect described herein, the Type A gelatin has a Bloom strength of about 150 grams to about 200 grams and the Type B gelatin has a Bloom strength of about 130 grams to about 170 grams. In another aspect described herein, the Type A gelatin or Type B gelatin comprises about 20% to about 32% of the total gel mass. In one aspect described herein, the one or more acid-insoluble polymers comprises about 5% to about 20% of the total gel mass. In another aspect described herein, the one or more acid-insoluble polymers comprises acrylic and methacrylate acid copolymers, cellulose acetate phthalate (CAP), cellulose acetate butyrate, hydroxypropylmethylcellulose phthalate (HPMCP), sodium alginate, pectin, or potassium alginate. In another aspect described herein, the one or more acrylic and methacrylate acid copolymers comprises: (a) poly(methacylic acid-co-ethyl acrylate) 1:1; or (b) poly(methacylic acid-co-ethyl acrylate) 1:1 and poly(ethyl acrylate-co-methyl methacrylate) 21; or (c) poly(methacylic acid-co-ethyl acrylate) 1:1 and poly(methyl acrylate-co-methyl methacrylate-co-methacrylic acid) 7:3:1; or (d) poly(methacylic acid-co-ethyl acrylate) 1:1, poly(ethyl acrylate-co-methyl methacrylate) 2:1, and poly(methyl acrylate-co-methyl methacrylate-co-methacrylic acid) 7:3:1. In one aspect described herein, the weight ratio of poly(methacylic acid-co-ethyl acrylate) 1:1 to poly(ethyl acrylate-co-methyl methacrylate) 2:1 is about 1:1 to about 44:1. In another aspect described herein, the weight ratio of poly(methacylic acid-co-ethyl acrylate) 1:1 to poly(methyl acrylate-co-methyl methacrylate-co-methacrylic acid) 7:3:1 is about 1:6 to about 5:1. In another aspect, the ratio of poly(methacylic acid-co-ethyl acrylate) 1:1 to poly(methyl acrylate-co-methyl methacrylate-co-methacrylic acid) 7:3:1 in the gel mass is about 7.5:3. In another aspect described herein, poly(methacylic acid-co-ethyl acrylate) 1:1 comprises about 2% to about 15% of the total gel mass. In another aspect described herein, poly(ethyl acrylate-co-methyl methacrylate) 2:1 comprises about 0.25% to about 4% of the total gel mass. In another aspect described herein, poly(methyl acrylate-co-methyl methacrylate-co-methacrylic acid) 7:3:1 comprises about 1% to about 14% of the total gel mass. In one aspect described herein, the one or more plasticizers comprise sorbitol, non-crystallizing sorbitol, corn syrup, maltitol, glycerol, polyethylene glycol, citric acid, citric acid esters, triethyl citrate, or combinations thereof. In another aspect described herein, the one or more plasticizers comprise glycerol, sorbitol, or triethyl citrate. In one aspect described herein, the total weight percentage of plasticizer comprises about 8% to about 30% of the total gel mass. In one aspect described herein, the alkali neutralizing agent is not present. In one aspect described herein, the alkali neutralizing agent is present. In another aspect described herein, the total weight percentage of alkali neutralizing agent comprises about 1% to about 7% of the total gel mass. In one aspect described herein, the alkali neutralizing agent comprises ammonium hydroxide, sodium hydroxide, or potassium hydroxide. In one aspect described herein, the gel mass composition comprises any of the following optional components: a gelling agent, an opacifier, a filler, a coloring, a flavoring, or a pharmaceutically acceptable excipient.

Another embodiment described herein is an oral enteric soft capsule shell formed from a gel mass composition comprising: (a) one or more types of gelatin; (b) one or more acid-insoluble polymers; (c) one or more plasticizers; (d) a solvent; and (e) optionally, an alkali neutralizing agent. In one aspect described herein, the gel mass composition comprises (a) gelatin comprises a Type A gelatin having a Bloom strength of about 175 to about 195 grams or a Type B gelatin having a Bloom strength of about 150 grams; (b) the one or more acid-insoluble polymers comprises poly (methacylic acid-co-ethyl acrylate) 1:1; (c) the one or more plasticizers comprises glycerol; (d) the optional alkali neutralizing agent comprises sodium hydroxide; and (e) the solvent comprises water.

Another embodiment described herein is an oral enteric soft capsule shell formed from a gel mass composition comprising: (a) acid bone Type A gelatin having a Bloom strength of 195 grams comprising about 27% of the total gel mass; (b) poly(methacylic acid-co-ethyl acrylate) 1:1 comprising about 11% of the total gel mass; (c) glycerol comprising about 18% of the total gel mass; (d) sodium hydroxide comprising about 3.5% of the total gel mass; and (e) water comprising about 40% of the total gel mass.

Another embodiment described herein is an oral enteric soft capsule shell formed from a gel mass composition comprising: (a) pig skin Type A gelatin having a Bloom strength of 175 grams comprising about 28% of the total gel mass; (b) poly(methacylic acid-co-ethyl acrylate) 1:1 comprising about 11% of the total gel mass; (c) glycerol comprising about 18% of the total gel mass; (d) sodium hydroxide comprising about 3.5% of the total gel mass; and (e) water comprising about 40% of the total gel mass.

Another embodiment described herein is an oral enteric soft capsule shell formed from a gel mass composition comprising: (a) lime bone Type B gelatin having a Bloom strength of 150 grams comprising about 28% of the total gel mass; (b) poly(methacylic acid-co-ethyl acrylate) 1:1 comprising about 11% of the total gel mass; (c) glycerol comprising about 18% of the total gel mass; (d) sodium hydroxide comprising about 3.5% of the total gel mass; and (e) water comprising about 40% of the total gel mass.

Another embodiment described herein is an oral enteric soft capsule shell formed from a gel mass composition comprising: (a) lime bone Type B gelatin having a Bloom strength of 150 grams comprising about 28% of the total gel mass; (b) poly(methacylic acid-co-ethyl acrylate) 1:1 comprising about 11% of the total gel mass; (c) glycerol comprising about 18% of the total gel mass; and (d) water comprising about 44% of the total gel mass.

Another embodiment described herein is an enteric soft capsule comprising any of the compositions described herein. In one aspect described herein, the enteric soft capsule comprises a matrix fill that is liquid, semi-solid, or solid. In another aspect described herein, the enteric soft capsule shell does not dissolve in simulated gastric fluid (pH 1.2) for at least 2 hours, and begins dissolution in simulated intestinal fluid (pH 6.8) within about 10 minutes. In one aspect described herein, the enteric soft capsule shell is clear or transparent. In one aspect described herein, the enteric soft capsule shell is transparent and colored.

Another embodiment described herein is a method for preparing an enteric soft capsule shell comprising: (a) combining dry shell components comprising a gelatin composition and an anionic polymer together to form a dry mixture; (b) adding plasticizer and solvent to the dry mixture with agitation to form a wet mixture; (c) heating the wet mixture with agitation and applying vacuum deaeration to form a gel mass; (d) heating the gel mass for an additional period; (e) forming an enteric soft capsule using rotary die technology; and (f) drying the enteric soft capsules.

Another embodiment described herein is an enteric soft capsule formed according to any of the methods described herein, wherein the final moisture content of the enteric soft capsule shell after the drying step is from about 5% to about 20%.

Another embodiment described herein is an enteric soft capsule formed according to any of the methods described herein comprising the enteric soft capsule composition of any of the compositions described herein. In one aspect described herein, the enteric soft capsule comprises an active ingredient in the matrix fill. In another aspect described herein, the enteric soft capsule shell is stable at pH 1.2 for at least 2 hours. In another aspect described herein, the enteric soft capsule shell dissolves at pH 6.8 within about 30 minutes. In another aspect described herein, the enteric soft capsule comprises a matrix fill that is liquid, semi-solid, or solid. In another aspect described herein, the enteric soft capsule shell is clear or transparent. In another aspect described herein, the enteric soft capsule shell is transparent and colored. In one aspect described herein, the thickness of the enteric soft capsule shell is from about 0.010 inches to about 0.050 inches.

Another embodiment described herein is a pharmaceutical composition comprising an enteric soft capsule comprising any of the compositions described herein.

Another embodiment described herein is a method for treating, ameliorating the symptoms of, or delaying the onset of a medical condition by providing a subject in need thereof with an enteric soft capsule comprising any of the compositions described herein and further comprising an active pharmaceutical ingredient or a nutraceutical.

DETAILED DESCRIPTION

Described herein are compositions and methods for manufacturing enteric soft capsules that have enhanced elasticity and enteric properties and are simple to manufacture.

As used herein, the terms "active ingredient," "active pharmaceutical ingredient," or "active pharmaceutical agent" refer to an agent, active ingredient, compound, or substance, compositions, or mixtures thereof, that provide a pharmacological, often beneficial, effect. Reference to a specific active ingredient includes, where appropriate, the active ingredient and any of its pharmaceutically acceptable salts or esters.

As used herein, the terms "dosage" or "dose" denote any form of the active ingredient formulation that contains an amount sufficient to produce a therapeutic effect with a single administration. The dosage form used herein is for oral administration. The preferred oral dosage forms are soft capsules or enteric soft capsules.

As used herein, the phrases "enteric soft capsule composition," "enteric soft capsule gel mass," "gel mass," or "enteric soft capsule shell" are used interchangeably and have the same meaning Typically, as used herein, "enteric soft capsule composition" or "gel mass" refer to enteric soft capsule compositions prior to forming the enteric soft capsule and "enteric soft capsule shell" refers to the enteric capsule shell after having been formed into an enteric soft capsule, for example, by using rotary die encapsulation.

The enteric soft capsule shell can comprise one or more types of gelatin, one or more acid-insoluble enteric polymers, one or more plasticizers, one or more solvents, and optionally colorings, gelling agents, flavorings, or other conventionally accepted pharmaceutical excipients or additives.

The enteric soft capsules described herein can be used for oral delivery of active pharmaceutical ingredients, nutraceuticals, or nutritionals that are irritating to the stomach, that are sensitive to the acidity of the stomach, or that have unpleasant tastes or odors. The enteric soft capsules described herein do not dissolve in the gastric environment (pH ca. 1.2), but readily dissolve in the intestinal environment (pH ca. 6.8).

Enteric soft capsules are described generally in International Patent Application Publication No. WO 2004/030658, U.S. Patent Application Publication No. US 2006/0165778, and U.S. Pat. No. 8,685,445, each of which is incorporated by reference herein for such teachings.

In one embodiment described herein, the pharmaceutical composition comprises an enteric soft capsule shell comprising a matrix fill further comprising an active pharmaceutical ingredient.

The enteric soft capsule shells described herein can comprise one or more film forming polymers, one or more enteric acid-insoluble polymers, one or more plasticizers, one or more solvents, optionally one or more alkali neutralizing agents, optionally one or more fillers, optionally one or more colorants, and optionally one or more flavorings and/or other conventionally accepted pharmaceutical excipients or additives.

Film-forming polymers that are useful for creating enteric soft capsule shells are gelatin, hydroxypropylmethylcellulose (HPMC), or carrageenan. In one aspect of the enteric soft capsule shell described herein, the film-forming polymer is gelatin. In one aspect of the enteric soft capsule shell described herein, the film-forming polymer is carrageenan.

Gelatin compositions that are useful for creating enteric soft capsules described herein can be classified as either Type A or Type B gelatin. Examples of gelatin compositions that are useful for creating enteric soft capsule shells as described herein comprise acid bone gelatin, pig skin gelatin, chicken skin gelatin, fish gelatin, acid hide gelatin, gelatin hydrolysate, lime bone gelatin or combinations thereof. Type A gelatin is derived from the acid hydrolysis of collagen (e.g., acid bone gelatin or pig skin gelatin), while Type B gelatin (e.g., lime bone gelatin) is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid processed gelatins form stronger gels than lime-processed gelatins of the same average molecular weight. In addition, at neutral pH values, Type A gelatins (acid processed gelatins) are typically net cationic and Type B gelatins (alkali processed gelatins) are typically net anionic. The strength of said gelatin compositions are often defined by their Bloom strength or grade in the range of about 30 Bloom to about 400 Bloom.

In one embodiment, film forming polymers that are useful for creating non-animal/non-gelatin enteric soft capsule shells are any form of carrageenan or mixture of carrageenan. In one aspect, kappa carrageenan, iota carrageenan, lambda carrageenan, or combinations thereof are useful for creating non-animal/non-gelatin enteric soft capsule shells.

Examples of enteric, acid-insoluble polymers or enteric polymers are acrylic and methacrylate acid copolymers, cellulose acetate phthalate (CAP), cellulose acetate butyrate, hydroxypropylmethylcellulose phthalate (HPMCP), algenic acid salts such as sodium or potassium alginate, or shellac. Acrylic and methacrylate acid copolymers are anionic copolymers based on methacrylic acid and methyl methacrylate that are particularly stable and are preferred in some embodiments. Acrylic and methacrylate acid copolymers available under the trade name EUDRAGIT® (Evonik Industries AG, Essen, Germany) are provided as powder or aqueous dispersions, and in one aspect, can be EUDRAGIT® L 30 D-55; EUDRAGIT® L 100-55; EUDRAGIT® L 100; EUDRAGIT® L 12.5; EUDRAGIT® S 100; EUDRAGIT® S 12.5; EUDRAGIT® FS 30 D; EUDRAGIT® E 100; EUDRAGIT® E 12.5; EUDRAGIT® E PO; EUDRAGIT® RL 100; EUDRAGIT® RL PO; EUDRAGIT® RL 30 D; EUDRAGIT® RL 12.5; EUDRAGIT® RS 100; EUDRAGIT® RS PO; EUDRAGIT® RS 30 D; EUDRAGIT® RS 12.5; EUDRAGIT® NE 30 D; EUDRAGIT® NE 40 D; EUDRAGIT® NM 30 D; other poly(meth)acrylate polymers; or a mixture thereof. Acid-insoluble polymer specifications are detailed in the United States Pharmacopoeia and in various monographs.

In one embodiment described herein, the enteric polymer in the enteric soft capsule shell comprises poly(methacylic acid-co-ethyl acrylate) 1:1 (e.g., EUDRAGIT® L 100-55). In one embodiment described herein, the enteric polymer comprises poly(ethyl acrylate-co-methyl methacrylate) 2:1 (e.g., EUDRAGIT® NE 40 D). In another embodiment described herein, the enteric polymer comprises poly(methyl acrylate-co-methyl methacrylate-co-methacrylic acid) 7:3:1 (e.g., EUDRAGIT® FS 30 D). In another embodiment described herein the enteric polymer comprises a combination of poly(methacylic acid-co-ethyl acrylate) 1:1 and poly (methyl acrylate-co-methyl methacrylate-co-methacrylic acid) 7:3:1. In another embodiment, the enteric polymer comprises a combination of poly(methacylic acid-co-ethyl acrylate) 1:1 and poly(ethyl acrylate-co-methyl methacrylate) 2:1. In another embodiment, the enteric polymer comprises a combination of poly(methacylic acid-co-ethyl acrylate) 1:1, poly(ethyl acrylate-co-methyl methacrylate) 2:1, and poly(methyl acrylate-co-methyl methacrylate-co-methacrylic acid) 7:3:1.

Plasticizers that are useful for creating enteric soft capsule shells as described herein are glycerol, sorbitol, polyethylene glycol, citric acid, citric acid esters, such as tri-ethyl citrate, or combinations thereof. The weight ratio between the film-forming polymer, the enteric acid-insoluble polymer, and plasticizer is adjusted so that the gel mass is flowable and not too viscous, and can be made into soft capsules using rotary die encapsulation methods. In one aspect, the plasticizer is glycerol. In one embodiment, the plasticizer is a mixture of glycerol and tri-ethyl citrate.

In one embodiment, enteric soft capsule shells can be made by dissolving the enteric acid-insoluble polymer in an aqueous solution of an alkali neutralizing agent such as ammonia, sodium hydroxide, potassium hydroxide, or liquid amines such as tri-ethanol amine or ethylene diamine. The amount of alkali is adjusted to give a final pH value of the gel mass less than or equal to about pH 9.0. In another embodiment, the final pH does not exceed 8.5. The film-forming polymer can then be combined with the plasticizer and solvent and then blended with the acid-insoluble gel to make a final homogeneous mixture. In one aspect, sodium hydroxide is a preferred alkali neutralizing agent.

In another embodiment described herein, an enteric soft capsule shell can be made by using an aqueous dispersion of the acid-insoluble polymer or polymers by adding alkaline materials such as ammonium, sodium, or potassium hydroxides, other alkalis, or a combination thereof that will cause the enteric acid-insoluble polymer to dissolve. The plasticizer-wetted, film-forming polymer can then be mixed with the solution of the acid-insoluble polymer. In one embodiment described herein, enteric acid-insoluble polymers in the form of salts of the above-mentioned bases or alkalis can be dissolved directly in water and mixed with the plasticizer-wetted, film-forming polymer. In another embodiment described herein, an aqueous dispersion of the acid-insoluble polymer or polymers can be used, which obviates the need for the addition of the aforementioned alkaline materials.

In one embodiment described herein, neutralization of the enteric acid-insoluble polymer with an alkali neutralizing agent is not required in the enteric soft capsule gel mass. In one aspect, gel mass compositions made with Type B gelatin unexpectedly do not require neutralization with an alkali neutralizing agent. In another aspect, the enteric properties of gel masses generated without an alkali neutralizing agent are superior to those generated with alkali neutralizing agents. Without being bound by any theory, it is thought that un-neutralized enteric acid-insoluble polymers, such as, methacrylic acid co-polymers (e.g., poly(methacylic acid-co-ethyl acrylate) 1:1) have more available carboxylic acid groups yielding a higher resistance to low pH gastric fluid. In another aspect, gel masses generated without an alkali neutralizing agent increase the compatibility of the gel mass with potential active pharmaceutical ingredients that are sensitive to the presence of alkali neutralizing agents.

In one embodiment, an enteric soft capsule shell has the composition of Table 1, including all possible iterations of the specified ranges that provide 100% of the total weight percentage, including or excluding the optional, excipients, opacifiers, colorants, sealants, and flavorings.

TABLE 1

Enteric Soft Capsule Shell Compositions

| Component | Exemplary Component | Composition Range (%) |
|---|---|---|
| Film-forming polymer | Gelatin (Type A and/or Type B) | Gel. 15-40 |
| Poly(methacylic acid-co-ethyl acrylate) 1:1 | EUDRAGIT ® L 100-55 | 2-15 |
| Poly(ethyl acrylate-co-methyl methacrylate) 2:1 | EUDRAGIT ® NE40D | 0.01-4 |
| Poly(methyl acrylate-co-methyl methacrylate-co-methacrylic acid) 7:3:1 | EUDRAGIT ® FS30D | 0.01-14 |
| Plasticizer | Glycerol, Triethyl citrate | 6-30 |
| Alkali neutralizing agents | NH$_4$OH (30%), NaOH, KOH | 0.01-7 |
| Filler (bulking agent) | Hydroxypropyl starch phosphate | 10-20 |
| Solvent | Water | 0.01-55 |
| Sealant (optional) | Kollicoat ® Protect | 1-5 |
| Opacifier | Titanium Dioxide | 1-7.5 |
| Colorant (optional) | Various | 0.05-1 |
| Flavoring (optional) | Various | 0.05-2 |
| Excipients (optional) | Various | 1-5 |

In one embodiment described herein, the weight percentage of film-forming polymer in the enteric soft capsule gel mass composition is about 1% to about 15% including all integers within the specified range. In another embodiment described herein, the weight percentage of film-forming polymer in enteric soft capsule gel mass composition is about 15% to about 40% including all integers within the specified range.

In one embodiment described herein, the weight percentage of the total gelatin composition in the enteric soft capsule gel mass composition is about 15% to about 40% including all integers within the specified range. In one aspect, the gelatin composition can comprise a Type A gelatin, a Type B gelatin, or a mixture thereof. In another embodiment, the weight percentage of the gelatin composition in the gel mass is about 20% to about 32% including all integers within the specified range. In another aspect, the weight percentage of the gelatin composition in the gel mass is about 22%. In another aspect, the weight percentage of the gelatin composition in the gel mass is about 26%. In another aspect, the weight percentage of the gelatin composition in the gel mass is about 28%. In another aspect, the weight percentage of the gelatin composition in the gel mass is about 30%.

In one embodiment described herein, the weight percentage of total film-forming carrageenan (e.g., a carrageenan composition) in the enteric soft capsule gel mass composition is about 1% to about 30%. In another embodiment, the weight percentage of the total carrageenan composition in the gel mass is about 3% to about 20%. In another embodiment, the weight percentage of the total carrageenan composition in the gel mass is about 3% to about 12%. In one aspect, the weight percentage of the total carrageenan composition in the gel mass is about 3%. In another aspect, the weight percentage of the total carrageenan composition in the gel mass is about 6%. In another aspect, the weight percentage of the total carrageenan composition in the gel mass is about 8%. In another aspect, the weight percentage of the total carrageenan composition in the gel mass is about 11%.

In another embodiment described herein, the weight percentage ratio range of iota carrageenan to kappa carrageenan in the enteric soft capsule gel mass composition is about 2.5:1 to about 5:1, including all integers within the specified range. In another embodiment, the weight percentage ratio range of iota carrageenan to kappa carrageenan in the gel mass is about 2.5:1 to about 4:1, including all integers within the specified range. In one aspect, the ratio of iota carrageenan to kappa carrageenan in the gel mass is about 4:1. In another aspect, the ratio of iota carrageenan to kappa carrageenan in the gel mass is about 3:1. In another aspect, the ratio of iota carrageenan to kappa carrageenan in the gel mass is about 3.5:1. In another aspect, the ratio of iota carrageenan to kappa carrageenan in the gel mass is about 3.8:1.

In another embodiment described herein, the weight percentage of iota carrageenan in the enteric soft capsule gel mass composition is about 0.5% to about 12%, including all integers within the specified range. In another embodiment, the weight percentage of iota carrageenan in the gel mass is about 2% to about 10%, including all integers within the specified range. In another embodiment, the weight percentage of iota carrageenan in the gel mass is about 2.5% to about 4%, including all integers within the specified range. In one aspect, the weight percentage of iota carrageenan in the gel mass is about 4%. In another aspect, the weight percentage of iota carrageenan in the gel mass is about 3%. In another aspect, the weight percentage of iota carrageenan in the gel mass is about 2.5%.

In one embodiment described herein, the weight percentage of kappa carrageenan in the enteric soft capsule gel mass composition is about 0.5% to about 4%, including all integers within the specified range. In another embodiment, the weight percentage of kappa carrageenan in the gel mass is about 0.5% to about 2.5%, including all integers within the specified range. In another embodiment, the weight percentage of kappa carrageenan in the gel mass is about 0.5% to about 1%, including all integers within the specified range. In one aspect, the weight percentage of kappa carrageenan in the gel mass is about 1%. In another aspect, the weight percentage of kappa carrageenan in the gel mass is about 0.8%. In another aspect, the weight percentage of kappa carrageenan in the gel mass is about 0.5%.

In one embodiment described herein, any carrageenan or mixture of carrageenan can be used to form the enteric soft capsules described herein.

In one embodiment described herein, at least one enteric acid-insoluble polymer is dispersed within the film-forming polymer gel mass that provides the total soft gel composition with enteric acid-insoluble properties, at relatively low concentrations of the enteric acid-insoluble polymer and without the need of excessive amounts of alkali, thus avoiding denaturation or degradation of the film-forming polymer that can weaken the integrity of the enteric soft capsule shell. In one aspect, the weight percentage of the total enteric acid-insoluble polymer content is from about 5% to about 20%.

In one embodiment described herein, the weight percentage of poly(methacylic acid-co-ethyl acrylate) 1:1 in the enteric soft capsule gel mass composition is about 2% to about 15%, including all iterations of integers within the specified range. In one aspect, the weight percentage of poly(methacylic acid-co-ethyl acrylate) 1:1 in the gel mass is about 6%. In another aspect, the weight percentage of poly(methacylic acid-co-ethyl acrylate) 1:1 in the gel mass is about 9%. In another aspect, the weight percentage of poly(methacylic acid-co-ethyl acrylate) 1:1 in the gel mass is about 11%. In another aspect, the weight percentage of poly(methacylic acid-co-ethyl acrylate) 1:1 in the gel mass is about 13%.

In one embodiment described herein, the weight percentage of poly(ethyl acrylate-co-methyl methacrylate) 2:1 in the enteric soft capsule gel mass is about 0.25% to about 4%, including all iterations of integers within the specified range. In one aspect, the weight percentage of poly(ethyl acrylate-co-methyl methacrylate) 2:1 in the gel mass is about 0.25%. In another aspect, the weight percentage of poly(ethyl acrylate-co-methyl methacrylate) 2:1 in the gel mass is about 2%. In another aspect, the weight percentage of poly(ethyl acrylate-co-methyl methacrylate) 2:1 in the gel mass is about 4%.

In one embodiment described herein, the weight percentage of poly(methyl acrylate-co-methyl methacrylate-co-methacrylic acid) 7:3:1 in the enteric soft capsule gel mass is about 1% to about 14%, including all iterations of integers within the specified range. In one aspect, the weight percentage of poly(methyl acrylate-co-methyl methacrylate-co-methacrylic acid) 7:3:1 in the gel mass is about 1%. In another aspect, the weight percentage of poly(methyl acrylate-co-methyl methacrylate-co-methacrylic acid) 7:3:1 in the gel mass is about 5%. In another aspect, the weight percentage of poly(methyl acrylate-co-methyl methacrylate-co-methacrylic acid) 7:3:1 in the gel mass is about 8%. In another aspect, the weight percentage of poly(methyl acrylate-co-methyl methacrylate-co-methacrylic acid) 7:3:1 in the gel mass is about 12%. In another aspect, the weight percentage of poly(methyl acrylate-co-methyl methacrylate-co-methacrylic acid) 7:3:1 in the gel mass is about 14%.

In one embodiment, the weight percentage range of total polymer content (i.e., film forming polymer and enteric polymer) of the enteric soft capsule gel mass described herein is about 10% to about 55%, including all integers within the specified range. In one aspect, the total polymer weight percentage of the gel mass is about 10%. In another aspect, the total polymer weight percentage of the gel mass is about 13%. In another aspect, the total polymer weight percentage of the gel mass is about 16%. In another aspect, the total polymer weight percentage of the gel mass is about 22%. In another embodiment, the weight percentage range of total polymer content of the enteric soft capsule gel mass described herein is about 25% to about 50%, including all integers within the specified range. In another aspect, the total polymer weight percentage of the gel mass is about 30%. In another aspect, the total polymer weight percentage of the gel mass is about 38%. In another aspect, the total polymer weight percentage of the gel mass is about 43%. In another aspect, the total polymer weight percentage of the gel mass is about 45%.

In one embodiment, the weight percentage range of total plasticizer in the enteric soft capsule gel mass is about 8% to about 30%, including all iterations of integers within the specified range. In one aspect, the total plasticizer weight percentage in the gel mass is about 19%. In another aspect, the total plasticizer weight percentage of the gel mass is about 14%. In another aspect, the total plasticizer weight percentage in the gel mass is about 18%. In another aspect, the total plasticizer weight percentage of the gel mass is about 23%.

In one embodiment, the alkali neutralizing-agent is ammonia (ammonium hydroxide; 30% w/v) that is added to comprise a weight percentage of about 1% to about 5% of the total enteric soft capsule gel mass. In one aspect, 30% w/v ammonia is added to comprise a weight percentage of about 2% of the gel mass. In another aspect, 30% w/v ammonia is added to a weight percentage of about 1.7% of the gel mass. In another aspect, ammonia is added to provide a final pH of about 9 in the enteric soft capsule gel mass. In another aspect, ammonia is added to provide a final pH of about 8.5 in the enteric soft capsule gel mass. In another aspect, after the capsules are filled and dried, the ammonia concentration is substantially reduced, owing to the fugitive nature of the volatile alkali. In another aspect, practically all of the ammonia is evaporated except for ammonium ions comprising salts with other moieties in the gel mass composition.

In one embodiment, the alkali neutralizing-agent is sodium hydroxide (NaOH 1 N) that is added to comprise a weight percentage of about 1% to about 7% of the total enteric soft capsule gel mass. In one aspect, 30% w/v ammonia is added to comprise a weight percentage of about 2% of the gel mass. In another aspect, 30% w/v ammonia is added to a weight percentage of about 3.5% of the gel mass.

In one embodiment, the weight ratio range of gelatin to enteric polymer in the enteric soft capsule gel mass is about 1.5:1 to about 6:1, including all iterations of ratios within the specified range. In one aspect, the ratio of gelatin to enteric polymer in the gel mass is about 2:1. In another aspect, the ratio of gelatin to enteric polymer in the gel mass is about 3:1. In another aspect, the ratio of gelatin to enteric polymer in the gel mass is about 4:1. In another aspect, the ratio of gelatin to enteric polymer in the gel mass is about 5:1.

In one embodiment, the weight ratio range of alkali neutralizing-agent to enteric polymer in the enteric soft capsule gel mass is about 1:14 to about 1:1.7, including all iterations of ratios within the specified range. In one aspect, the ratio of alkali neutralizing-agent to enteric polymer in the gel mass is about 5:1. In another aspect, the ratio of alkali neutralizing-agent to enteric polymer in the gel mass is about 1:6. In another aspect, the ratio of alkali neutralizing-agent to enteric polymer in the gel mass is about 1:4. In another aspect, the ratio of alkali neutralizing-agent to enteric polymer in the gel mass is about 1:3.

In one embodiment, the weight ratio of gelatin to plasticizer in the enteric soft capsule gel mass is about 1:1 to 3:1, including all iterations of ratios within the specified range. In one aspect, the weight ratio of gelatin to plasticizer in the gel mass is about 1:1. In another aspect, the weight ratio of gelatin to plasticizer in the gel mass is about 2:1. In another aspect, the weight ratio of gelatin to plasticizer in the gel mass is about 3:1.

In one embodiment, the weight ratio of plasticizer to enteric polymer in the enteric soft capsule gel mass is about 1:1 to 3:1, including all iterations of ratios within the specified range. In one aspect, the weight ratio of plasticizer to enteric polymer in the gel mass is about 1:1. In another aspect, the weight ratio of plasticizer to enteric polymer in the gel mass is about 1.7:1. In another aspect, the weight ratio of plasticizer to enteric polymer in the gel mass is about 3:1.

In one embodiment, the weight ratio range of poly(methacylic acid-co-ethyl acrylate) 1:1 to total enteric polymer in the enteric soft capsule gel mass is about 1:7 to about 1:1. In one aspect, the weight ratio of poly(methacylic acid-co-ethyl acrylate) 1:1 to total enteric polymer in the enteric soft capsule gel mass is about 1:1.

In one embodiment, the weight ratio range of poly(ethyl acrylate-co-methyl methacrylate) 2:1 to total enteric polymer in the enteric soft capsule gel mass is about 1:50 to about 1:4. In one aspect, the weight ratio of poly(ethyl acrylate-co-methyl methacrylate) 2:1 to total enteric polymer in the enteric soft capsule gel mass is about 1:50.

In one embodiment, the weight ratio range of poly(methyl acrylate-co-methyl methacrylate-co-methacrylic acid) 7:3:1 to total enteric polymer in the enteric soft capsule gel mass is about 1:6 to about 1:1. In one aspect, the weight ratio of poly(methyl acrylate-co-methyl methacrylate-co-methacrylic acid) 7:3:1 to total enteric polymer in the enteric soft capsule gel mass is about 1:1.3.

In one embodiment, the weight ratio range of poly(methacylic acid-co-ethyl acrylate) 1:1 to poly(ethyl acrylate-co-methyl methacrylate) 2:1 in the enteric soft capsule gel mass is about 1:1 to about 44:1, including all iterations of ratios within the specified range. In one aspect, the weight ratio of poly(methacylic acid-co-ethyl acrylate) 1:1 to poly(ethyl acrylate-co-methyl methacrylate) 2:1 in the enteric soft capsule gel mass is about 44:1.

In one embodiment, the weight ratio range of poly(methacylic acid-co-ethyl acrylate) 1:1 to poly(methyl acrylate-co-methyl methacrylate-co-methacrylic acid) 7:3:1 in the enteric soft capsule gel mass is about 1:6 to about 5:1, including all iterations of ratios within the specified range. In one aspect, the weight ratio of poly(methacylic acid-co-ethyl acrylate) 1:1 to poly(methyl acrylate-co-methyl methacrylate-co-methacrylic acid) 7:3:1 in the enteric soft capsule gel mass is about 1:4. In another aspect, the ratio of poly(methacylic acid-co-ethyl acrylate) 1:1 to poly(methyl acrylate-co-methyl methacrylate-co-methacrylic acid) 7:3:1 in the gel mass is about 4:1. In another aspect, the ratio of poly(methacylic acid-co-ethyl acrylate) 1:1 to poly(methyl acrylate-co-methyl methacrylate-co-methacrylic acid) 7:3:1 in the gel mass is about 7.5:3.

In one embodiment, the weight ratio range of total plasticizer to total polymer (film forming and enteric polymer) in the enteric soft capsule gel mass is about 1:4 to about 1:1, including all iterations of ratios within the specified range. In one aspect, the weight ratio range of total plasticizer to total polymer in the gel mass is about 1:4. In another aspect, the weight ratio range of total plasticizer to total polymer in the gel mass is about 1:3. In another aspect, the weight ratio range of total plasticizer to total polymer in the gel mass is about 1:2. In another aspect, the weight ratio range of total plasticizer to total polymer in the gel mass is about 1:1.

In one embodiment, the solvent comprises about 0.01% to about 40% of the enteric soft capsule, including all integers within the specified range. In one embodiment, the solvent is water. The quantity of water in the composition varies depending on the quantities of the other ingredients. For example, the quantity of opacifier, colorant, flavoring, or other excipients can change the percentage of water present in the composition. In one embodiment, the weight percentage of water is as much as suffices to bring the total weight percentage to 100% (i.e., quantum sufficiat; q.s.). In another embodiment, the water comprises about 5%, about 10%, about 15%, about 20%, about 25%, about 30%, about 35%, or about 40% of the enteric soft capsule composition. In another embodiment, water comprises about 20% to about 30% of the enteric soft capsule composition, including all iterations of integers within the specified range. In one embodiment, water comprises about 28% of the enteric soft capsule composition.

In one embodiment, the final moisture (water) content of the enteric soft capsule is from about 5% to about 20%, including all integers within the specified range. In another embodiment, the moisture content of the enteric soft capsule is about 8% to about 12%, including all integers within the specified range. In one aspect, the final moisture content of the enteric soft capsule is about 8%. In another aspect, the final moisture content is about 9%. In another aspect, the final moisture content of the enteric soft capsule is about 10%. In another aspect, the final moisture content of the enteric soft capsule is about 11%. In another aspect, the final moisture content of the enteric soft capsule is about 12%.

In one embodiment, the enteric soft capsule gel masses described herein, are unexpectedly more flowable and less viscous than soft capsule gel masses generated with structurally similar poly(methacylic acid-co-methyl methacrylate) anionic copolymers (e.g., poly(methacylic acid-co-methyl methacrylate) 1:1). In one aspect, the aforementioned above gel masses result in enteric soft capsules that are less brittle and more efficiently generated through rotary die encapsulation methods known in the art.

In another embodiment described herein, enteric soft capsule gel masses can be generated to be even less viscous and more flowable with a combination of poly(methacylic acid-co-ethyl acrylate) 1:1 and poly(ethyl acrylate-co-methyl methacrylate) 2:1.

In another embodiment described herein, enteric soft capsules generated from gel masses comprising poly(methacylic acid-co-ethyl acrylate) 1:1 and poly(methyl acrylate-co-methyl methacrylate-co-methacrylic acid) 7:3:1 as described herein comprise modified release profiles (e.g., release at pH greater than 7.0 or colonic release). In one aspect, the ratio of poly(methacylic acid-co-ethyl acrylate) 1:1 to poly(methyl acrylate-co-methyl methacrylate-co-methacrylic acid) 7:3:1 in the enteric soft capsule shell gel mass is adjusted to determine the location in the gastro-intestinal tract where capsule shell dissolution occurs. In another aspect, ratios of poly(methacylic acid-co-ethyl acrylate) 1:1 to poly(methyl acrylate-co-methyl methacrylate-co-methacrylic acid) 7:3:1 of at least about 1:3 or greater in the gel mass promote capsule shell dissolution at higher pH values.

In one embodiment, the enteric soft capsule shell has the exemplary composition shown in Table 2.

TABLE 2

Exemplary Enteric Soft Capsule Shell Composition

| Component | Percent weight (%) |
| --- | --- |
| Gelatin (Lime bone gelatin 150B1) | 27.8 |
| Poly(methacylic acid-co-ethyl acrylate) 1:1 (EUDRAGIT ® L 100-55) | 10.8 |
| Glycerol | 17.8 |
| Sodium hydroxide | 3.5 |
| Water | 40 |
| TOTAL | 100% |

Components and Relational Ratios

| | |
| --- | --- |
| Final pH | 4.0-9.0 |
| Total polymer (total enteric + gelatin) | 38.6 |
| Ratio gelatin to total enteric | 2.6 |
| Ratio gelatin to plasticizer | 0.64 |
| Ratio plasticizer to total polymer | 0.46 |
| Ratio plasticizer to total enteric | 1.65 |
| Ratio neutralizer to total enteric | 0.32 |

In one embodiment, the enteric soft capsule shell comprises about 28% Type A gelatin; about 11% poly(methacylic acid-co-ethyl acrylate) 1:1; about 18% glycerol; about 3.5% sodium hydroxide; and about 40% water.

In one embodiment, the enteric soft capsule shell comprises about 28% Type B gelatin; about 11% poly(methacylic acid-co-ethyl acrylate) 1:1; about 18% glycerol; and about 44% water.

In one embodiment, the enteric soft capsule shell does not dissolve or disintegrate in acids, such as 0.1 N hydrochloric acid or simulated gastric fluid (ca. pH 1.2), despite the fact that the majority of the shell ingredients (i.e., greater than 50%) normally dissolve in, or are miscible with, acids. In another embodiment, the enteric soft capsules made using the compositions described herein remain intact in hydrochloric acid or simulated gastric fluid for at least two hours and the capsules readily release their contents upon shifting the pH of the solution to ca. 6.8, such as that of simulated intestinal fluid. In one aspect, the enteric soft capsule is resistant to dissolution at about pH 1.2 for at least about 2 hours. In another aspect, the enteric soft capsule begins dissolution at pH of about 6.8 within about 10 minutes.

In another embodiment, the final enteric capsule composition provides films of increased strength without substantially compromising film elasticity. Moreover, films made from the enteric soft capsule compositions as described herein can be sealed at normal temperature range typically used for making traditional soft gel capsules. In one aspect, enteric soft capsules are made using a rotary die apparatus as described in U.S. Pat. Nos. 5,459,983; 5,146,730; and 6,482,516, each of which are incorporated by reference herein for such teachings.

Another embodiment described herein includes a process of manufacturing enteric soft capsules comprising the pharmaceutical composition as described herein. The process includes preparing a gel mass composition comprising a film-forming, water-soluble polymer and an enteric acid-insoluble polymer and mixing with appropriate plasticizers and solvent; casting the gel mass into films or ribbons using heat-controlled drums or surfaces; and manufacturing a soft capsule comprising a matrix fill using rotary die technology. The thickness of the films or ribbons that form the enteric capsule shell is from about 0.010 inches (≈0.254 mm) to about 0.050 inches (≈21.27 mm), including all integers within the specified range. The shell thickness can be about 0.010 inch (≈0.254 mm), about 0.015 inch (≈0.381 mm), about 0.02 in (≈0.508 mm), about 0.03 in (≈0.762 mm), about 0.04 in (≈21.02 mm), or about 0.05 in (≈21.27 mm). In one embodiment, the thickness is about 0.02 inches (≈0.508 mm) to about 0.040 inches (≈21.02 mm). In one embodiment, the shell thickness is about 0.028 inches (≈0.711 mm). In another embodiment, the shell thickness is about 0.033 inches (≈0.838 mm). In another embodiment, the shell thickness is about 0.038 inches (≈0.965 mm).

The enteric soft capsules described herein can contain a matrix fill that is liquid, semi-solid, or solid. Capsules prepared as described herein can contain a hydrophobic solution or suspension, such as vegetable oils or shortening, soybean oils, or waxes, or combinations thereof. The matrix fill can be formulated to prevent interaction with the enteric soft capsule shell components and release the pharmaceutical composition at a specified rate.

The fill can comprise one or more active ingredients and, optionally, one or more pharmaceutically acceptable excipients, colors, or flavorings.

Suitable active ingredients can include, for example, active pharmaceutical ingredients (e.g., therapeutic agents, prophylactic agents, and diagnostic agents), nutraceuticals, vitamins, minerals, and combinations thereof.

In one embodiment, active ingredients can include, for example, active pharmaceutical ingredients (e.g., therapeutic agents, prophylactic agents, and diagnostic agents), nutraceuticals, fish oils, that for example, are administered to a human or a human in need thereof. In one aspect, the human subject or a human subject in need thereof is a medical patient.

One embodiment described herein is a pharmaceutical composition comprising an enteric soft capsule as described herein comprising an active pharmaceutical ingredient or plurality of active pharmaceutical ingredients.

The matrix fill can optionally include one or more pharmaceutically acceptable excipients. Examples of pharmaceutically acceptable excipients include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinyl pyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), and PLURONICS™ (BASF; Florham Park, N.J.). Diluents commonly used in the art can also be encapsulated within the shell, including water or other solvents, solubilizing agents, and emulsifiers, as for example, ethyl alcohol, isopropyl alcohol, ethyl carbonate, ethyl acetate, benzyl alcohol, benzyl benzoate, 1,3-butylene glycol, dimethylformamide, oils, in particular, cottonseed oil, groundnut oil, corn germ oil, olive oil, castor oil, sesame oil, glycerol, tetrahydrofurfuryl alcohol, and fatty acid esters of sorbitan, and mixtures of these substances.

Exemplary lipid or lipophilic liquid or semi-solid lipophilic substance useful for matrix fills include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; and partially hydrogenated oils; bees wax; polyethoxylated bee's wax; paraffin; normal waxes; medium chain medium chain monoglycerides; diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; dicaprylate; monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

Additional solubility enhancing agents useful for the matrix fills include Capmul® MCM, Captex® 355, Cremophor® RH 40, Croscarmellose, Crospovidone, Crospovidone CL, Crospovidone CL-F, Crospovidone CL-M, Imwitor® 742, Kollidon® CL, Kollidon® CL-F, Kollidon® CL-M, Labrafac™ Lipophile WL 1349, Labrafil® M2125CS, Labrasol®, Lutrol® F 68, Maisine™ 35-1, mannitol, Miglyol® 812, Pearlitol® Flash, Peceol®, polyethylene glycol 400, polyethylene glycol 600, polyethylene glycol 3350, Plurol® Oleique CC 497, Povidone K 17, Povidone K 30, and sodium lauryl sulfate.

Additional pharmaceutical excipients useful for matrix fills include, for example, the following: Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Alkalizing agents (ammonia solution, ammonium carbonate, diethanolamine, diisopropanolamine, potassium hydroxide, sodium bicarbonate, sodium borate, sodium carbonate, sodium hydroxide, trolamine); Antifoaming agents (dimethicone, simethicone); Antimicrobial preservatives (benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); a Wetting agent, such as lecithin; Emulsifying and/or solubilizing agents (acacia, cholesterol, diethanolamine (adjunct), glyceryl monostearate, lanolin alcohols, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, diacetate, monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, sorbitol); Plasticizers (e.g., castor oil, diacetylated monoglycerides, diethyl phthalate, glycerin, mono- and di-acetylated monoglycerides, propylene glycol, triacetin, triethyl citrate); polymers (e.g., cellulose acetate, alkyl celluloses, hydroxyalkyl, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, propylene carbonate, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (Bacteriostatic water for injection, bacteriostatic sodium chloride injection); Viscosity-increasing (see suspending agent); Water repelling agent (cyclomethicone, dimethicone, simethicone); and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol). This list is not meant to be exclusive, but instead merely representative of the classes of excipients and the particular excipients that may be used in oral dosage forms as described herein.

In one embodiment, the matrix fill can include a release regulator such as a fatty acid salt, fatty acid ester, or fatty acid polyoxyethylene derivative. The release regulator can also be a surfactant having a hydrophilic/lipophilic balance (HLB) value between about 2 and about 40. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993), which is incorporated by reference herein for such teachings.

In one embodiment, the matrix fill may include one or more hydrophilic carriers. Examples of hydrophilic carriers are all natural, synthetic, or semi-synthetic products, which can be defined as aqueous carriers not mixable or only partially mixable with oil. All components can be used alone or if possible in mixtures with different percentages. Among aqueous components which can be used as a dispersing phase or also as a dispersed phase.

Examples of aqueous solutions of hydrophilic polymers, which are hydrosoluble or hydrodispersable of various nature, such as polyethylenglycol, polyvinyl pyrrolidone, polyacrylic acids and derivatives, such as Carbopol® 971, polymethacrylic acids polyoxyethylenepolyoxypropylene copolymers (for example Poloxamer®, Lutrol™), hydrophilic polysaccharides of various nature, for example dextran, xanthan, scleroglucan, arabic gum, guar gum, chitosan, cellulose and starch derivatives.

In one embodiment, the matrix fill can include a neutralizing agent. Without being bound to any theory, the neutralizing agent is thought to stabilize the active pharmaceutical ingredient in the matrix fill by preventing hydrolysis. In addition, without being bound by any theory, it is also thought that the neutralizing agent stabilizes the enteric soft capsule shell by forming salts with the methylacrylate moieties from the enteric soft capsule shell. In one aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, esters or salts thereof, or combinations thereof.

In one embodiment, the lipid or lipophilic vehicle comprises a liquid lipophilic vehicle and a semisolid lipophilic vehicle. In one embodiment, the liquid lipid or lipophilic vehicle can be olive oil, sunflower oil, canola oil, palmitoleic acid, oleic acid, myristoleic acid, linoleic acid, arachidonic acid, paraffin oil, or mineral oil. In another embodiment, the semi-solid lipophilic vehicle can be a polyethylene glycol glyceride ester, paraffin wax, or bees wax. In another embodiment, the semi-solid lipophilic vehicle is Gelucire® 33/01, Gelucire® 37/02, Gelucire® 39/01, Gelucire® 43/01, Gelucire® 44/14, Gelucire® 50/02, Gelucire® 50/13, Gelucire® 53/10, or Gelucire® 62/02. In one aspect, the liquid lipid or lipophilic vehicle is olive oil. In another aspect, the semisolid lipid or lipophilic vehicle comprises a Gelucire®. In another aspect, the Gelucire® semisolid lipid vehicle has a HLB value of about 1 and a melting point of about 43. In another aspect, the semisolid lipid or lipophilic vehicle is Gelucire® 43/01.

In another embodiment, the matrix comprises a hydrophilic ionic polymer. In one embodiment, the hydrophilic polymers comprise polyhydroxylalkylenediamine, dimethylaminoethyl methacrylate copolymer, Poly(butyl methacrylate-co-(2-dimethylaminoethyl)methacrylate-co-(2-dimethylaminoethyl) 1:2:1 (Eudragit® EPO); sodium carboxy methylcellulose, carboxymethyl cellulose ethylenediamine, sodium alginate, alginic acid, pectin, carbomers, Carbopol® copolymers, such as Carbopol® 934, Carbopol® 940, Carbopol® 941 or Carbopol® 974P; a Pemulen® polymer; polycarbophil poly galacturonic acid, polyglucoronic acid, chondroitic sulfate, carrageenan, and acrylic methacrylate copolymers. In one aspect, the hydrophilic polymer swells in aqueous media. In another aspect, the hydrophilic polymers swell at a pH of about 4 to about 6. In another embodiment, one or more hydrophilic ionic polymers form ionic interactions. In another embodiment, the matrix comprises anionic polymers, cationic polymers, or mixtures thereof. In another embodiment, a hydrophilic cationic polymer and a hydrophilic anionic polymer are combined to form an ionic polymer complex or network. In one aspect, the hydrophilic polymer is Carbopol® 971A. In another aspect, the hydrophilic polymer is Eudragit® EPO.

In another embodiment, the matrix comprises a non-ionic surfactant. The surfactant can have a hydrophilic/lipophilic balance (HLB) value between about 1 and about 25 and a melting point between about 25° C. and about 70° C. The HLB characteristic of surfactants can be determined in accordance with "Physical Pharmacy: Physical Chemical Principles in the Pharmaceutical Sciences," Fourth Edition, pp. 371-373, A. Martin, Ed., Lippincott Williams & Wilkins, Philadelphia (1993). Suitable non-ionic surfactants include: Pluronic® 10R5, Pluronic® 17R2, Pluronic® 17R4, Pluronic® 25R2, Pluronic® 25R4, Pluronic® 31R1, Pluronic® F 108, Pluronic® F 108 NF, Pluronic® F 108, Pluronic® F 108NF, Poloxamer 338, Pluronic® F 127, Pluronic® F 127 NF, Pluronic® F 127 NF 500 BHT Prill, Pluronic® F 127 NF Prill, Poloxamer 407, Pluronic® F 38, Pluronic® F 38 Pastille, Pluronic® F 68, Pluronic® F 68 LF Pastille, Pluronic® F 68 NF, Pluronic® F 68 NF Prill, Poloxamer 188, Pluronic® F 68 Pastille, Pluronic® F 77, Pluronic® F 77 Micropastille, Pluronic® F 87, Pluronic® F 87 NF, Pluronic® F 87 NF Prill, Poloxamer 237, Pluronic® F 88, Pluronic® F 88 Pastille, Pluronic® F 98, Pluronic® L 10, Pluronic® L 101, Pluronic® L 121, Pluronic® L 31, Pluronic® L 35, Pluronic® L 43, Pluronic® L 61, Pluronic® L 62, Pluronic® L 62 LF, Pluronic® L 62D, Pluronic® L 64, Pluronic® L 81, Pluronic® L 92, Pluronic® N 3, Pluronic® P 103, Pluronic® P 104, Pluronic® P 105, Pluronic® P 123 Surfactant, Pluronic® P 65, Pluronic® P 84, Pluronic® P 85, Adogen® 464, Alkanol® 6112, Brij® 52, Brij® 93, Brij® S2, Brij® S, Brij® 58, Brij® C10, Brij® L4, Brij® O10, Brij® O10, BRIJ® O20, Brij® S10, Brij® S20, ethylenediamine tetrakis(ethoxylate-block-propoxylate)tetrol, ethylenediamine tetrakis(ethoxylate-block-propoxylate)tetrol, ethylenediamine tetrakis(propoxylate-block-ethoxylate)tetrol, IGEPAL® CA-210, IGEPAL® CA-520, IGEPAL® CA-720, IGEPAL® CO-520, IGEPAL® CO-630, IGEPAL® CO-720, IGEPAL® CO-890, IGEPAL® DM-970, MERPOL® DA, MERPOL® HCS, MERPOL® OJ, MERPOL® SE, MERPOL® SH, MERPOL® A, Poly(ethylene glycol)sorbitan tetraoleate, poly(ethylene glycol) sorbitol hexaoleate, poly(ethylene glycol) (12), poly(ethylene glycol) (18), polyethylene-block-poly(ethylene glycol), sorbitan monopalmitate, 2,4,7,9-tetramethyl-5-decyne-4,7-diol ethoxylate, Nonidet™ P-40, Triton™ N-101, Triton™ X-100, Triton™ X-114, Triton™ X-405, TWEEN® 20, TWEEN® 40, TWEEN® 60, TWEEN® 85, Zonyl® FS-300, or Zonyl® FSN. In one embodiment, the non-ionic surfactant comprises Pluronic® F127, Tween 80, Span 80, IGEPAL®, or Triton™ X-100. In one aspect, the non-ionic surfactant comprises a poloxamer. In another aspect, the non-ionic surfactant comprises Pluronic® F127.

In another embodiment, the matrix comprises a hygroscopic polymer. In one embodiment, the hygroscopic polymers include polyvinylpyrrolidone, copovidone, hydroxypropylmethylcellulose, hydroxypropylcellulose, ethyl cellulose, methylcellulose, and polyethylene oxide. Suitable hygroscopic polymers include polyvinyl alcohol, a copolymer of polyvinylpyrrolidone and polyvinyl acetate, hydroxypropyl cellulose, hydroxypropyl methylcellulose, hydroxyethyl cellulose, hydroxymethyl cellulose, gelatin, polyethylene oxide, acacia, dextrin, starch, polyhydroxyethylmethacrylate, a water-soluble non-ionic polymethacrylate or copolymer thereof, a modified cellulose, a modified polysaccharide, a non-ionic gum, or a non-ionic polysaccharide. In one aspect, the hygroscopic polymer is polyvinylpyrrolidone. In another aspect, the hygroscopic polymer comprises Kollidon® 90 F.

In another embodiment, the matrix comprises a pH buffering agent. Suitable pharmaceutically acceptable buffering agents comprise arginine, aminomethyl propanol, tetrahydroxypropyl ethylenediamine, triethanolamine, tromethamine, PEG-15 cocamine, di-isopropanol amine, tri-isopropanol amine, N-methyl-D-glucamine, glycine, malate, tartarate, lactate, citrate, acetate, sodium bicarbonate, sodium phosphate, or other buffering agents, having $pK_a$s at any physiologically acceptable pH, generally from about pH 4 to about pH 7. Amino acids or other physiological metabolites may be used as buffering agents. A combination of buffering agents may also be employed, such as phosphate and acetate, and the like. In one aspect, the pH buffering agent is N-methyl-D-glucamine (e.g., meglumine).

In another embodiment, the matrix comprises a neutralizing agent. Suitable pharmaceutically acceptable neutralizing agents comprise HCl, phosphoric acid, carbonic acid, sodium hydroxide, ammonium hydroxide, potassium hydroxide, sodium bicarbonate, sodium carbonate, and the like.

In another embodiment, the active pharmaceutical ingredient can be dispersed in the internal phase as a suspension form. In another embodiment, the active pharmaceutical ingredient can be dispersed in the internal phase as a solid form.

In one embodiment described herein, the matrix may comprise one or more lipid or lipophilic vehicles, one or more hydrophilic polymers, one or more non-ionic surfactants, one or more hygroscopic polymers, one or more pH buffering agents, and one or more active pharmaceutical ingredients. Without being bound to any theory, it is believed that the hydrophilic cationic and anionic polymers described herein combine within the matrix to form polymer networks or complexes comprising ionic interactions. Further, without being bound to any theory, it is believed that the ionic polymer network swells when hydrated with an aqueous solution and the swelling impedes the dissolution and/or diffusion of the active pharmaceutical ingredient out of the matrix. Without being bound by any theory, it is believed that non-ionic surfactants and hygroscopic polymers facilitate hydration of the hydrophilic ionic polymers described herein. Moreover, without being bound to any theory, the lipid or lipophilic vehicle of the matrix further prevents diffusion and/or solvation of the active pharmaceutical ingredient. The matrix compositions described herein permit abuse deterrence by preventing liberation of the active ingredient for injection or insufflation and prevent solvation, dissolution, or extraction of the active pharmaceutical ingredient by use of aqueous or organic solutions. Furthermore, the matrix compositions also provide controlled release delivery of the active pharmaceutical ingredient after ingestion by a subject.

In another embodiment, the lipid or lipophilic vehicle comprises a liquid lipid or lipophilic vehicle, a semisolid lipid or lipophilic vehicle, or a mixture thereof.

Exemplary lipid or lipophilic substances include mineral oil; light mineral oil; natural oils (e.g., vegetable, corn, canola, sunflower, soybean, olive, coconut, cocoa, peanut, almond, cottonseed, persic, sesame, squalane, castor, cod liver, etc) hydrogenated vegetable oil; partially hydrogenated oils; beeswax; polyethoxylated beeswax; paraffin; normal waxes; medium chain medium chain monoglycerides, diglycerides and triglycerides; higher aliphatic alcohols; higher aliphatic acids; long chain fatty acids; saturated or unsaturated fatty acids; hydrogenated fatty acids; fatty acid glycerides; polyoxyethylated oleic glycerides; monoglycerides and diglycerides; mono-, bi- or tri-substituted glycerides; glycerol mono-oleate esters; glycerol monocaprate; glyceryl monocaprylate; propylene glycol dicaprylate; propylene glycol monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty alcohols associated with polyethoxylate fatty alcohols; cetyl alcohol; octyldodecanol; myristyl alcohol; isopropyl myristate, isopropyl palmitate, stearic acid, stearyl alcohol, and others known in the art.

In one embodiment, the matrix can include a neutralizing agent. Without being bound to any theory, it is thought that lactic acid stabilizes the enteric soft capsule shell by forming salts with the methylacrylate moieties from the capsule shell. In one aspect, the neutralizing agent comprises an organic acid, ester, or salt. In another aspect, the neutralizing agent comprises at least one of lactate, fumarate, caprylate, caprate, oleate, maleate, succinate, tartrate, citrate, glutamate, gluconate, esters or salts thereof, or combinations thereof.

In one embodiment, the matrix can include a hydrophilic internal phase and a lipid or lipophilic external phase. The internal phase can include polypropylene glycol or polyethylene glycol of molecular weight ranging from about 200 to about 8000. In one another embodiment, the internal phase can include hydroalcoholic solutions of cellulose derivatives, polyacrylates, polyvinyl polymers, or combinations thereof.

In one embodiment, the internal phase can include polymers such as methylcellulose, hydroxypropylmethylcellulose, polymethylmethacrylate, or polyvinylpyrrolidone (PVP). The internal phase can also be structured. A "structured" internal phase, as used herein, means a solid, semisolid, or a gel whose shape is relatively stable and does not usually aggregate to form a large globule. A structured internal phase therefore provides controlled drug release and stabilizes the physical state of the matrix. Without being bound by any theory, it is believed that the structured nature of the matrix impedes solvation and/or diffusion of the active ingredient out of the matrix. In one another embodiment, the external phase can include a vegetable oil, hydrogenated vegetable oil, fatty acid, fatty acid ester, wax, or a combination thereof. In one another embodiment, the active ingredient can be dispersed in the internal phase as a suspension form.

Examples of active pharmaceutical ingredients that can be included comprise agents classified as, for example, an adrenocortical steroid, adrenocortical suppressant, aldosterone antagonist, amino acid, anabolic steroid, androgen, antagonist, anthelmintic, anti-acne agent, anti-adrenergic, anti-allergic, anti-amebic, anti-androgen, anti-anemic, anti-anginal, anti-arthritic, anti-asthmatic, anti-atherosclerotic, antibacterial, anticholelithic, anticholelithogenic, anticholinergic, anticoagulant, anticoccidal, antidiabetic, antidiarrheal, antidiuretic, antidote, anti-estrogen, antifibrinolytic, antifungal, antiglaucoma agent, antihemophilic, antihemorrhagic, antihistamine, antihyperlipidemic, antihyperlipoproteinemic, antihypertensive, antihypotensive, anti-infective, anti-infective, anti-inflammatory, antikeratinizing agent, antimalarial, antimicrobial, antimitotic, antimycotic, antineoplastic, antineutropenic, antiparasitic, antiperistaltic, antipneumocystic, antiproliferative, antiprostatic hypertrophy, antiprotozoal, antipruritic, antipsoriatic, antirheumatic, antischistosomal, antiseborrheic, antisecretory, antispasmodic, antithrombotic, antitussive, anti-ulcerative, anti-urolithic, antiviral, appetite suppressant, benign prostatic hyperplasia therapy agent, bone resorption inhibitor, bronchodilator, carbonic anhydrase inhibitor, cardiac depressant, cardioprotectant, cardiotonic, cardiovascular agent, choleretic, cholinergic, cholinergic agonist, cholinesterase deactivator, coccidiostat, contrasting agent, diagnostic aid, diuretic, ectoparasiticide, enzyme inhibitor, estrogen, fibrinolytic, free oxygen radical scavenger, glucocorticoid, gonad-stimulating principle, hair growth stimulant, hemostatic, hormone, hypocholesterolemic, hypoglycemic, hypolipidemic, hypotensive, imaging agent, immunizing agent, immunomodulator, immunoregulator, immunostimulant, immunosuppressant, impotence therapy adjunct, inhibitor, keratolytic, LHRH agonist, liver disorder treatment, luteolysin, mucolytic, mydriatic, nasal decongestant, neuromuscular blocking agent, non-hormonal sterol derivative, nonsteroidal anti-inflammatory drugs, oxytocic, plasminogen activator, platelet activating factor antagonist, platelet aggregation inhibitor, potentiator, progestin, prostaglandin, prostate growth inhibitor, prothyrotropin, radioactive agent, regulator, relaxant, repartitioning agent, scabicide, sclerosing agent, selective adenosine A1 antagonist, steroid, suppressant, symptomatic multiple sclerosis, synergist, thyroid hormone, thyroid inhibitor, thyromimetic, amyotrophic lateral sclerosis agents, Paget's disease agents, unstable angina agents, uricosuric, vasoconstrictor, vasodilator, vulnerary, wound healing agent, and xanthine oxidase inhibitor. Further examples of suitable pharmaceutical ingredients include those as listed in the Merck Index (13$^{th}$ Edition, Wiley, 2001), The United States Pharmacopeia-National Formulary (USP-NF), and the FDA's Orange book, which are each incorporated by reference herein for their teachings of pharmaceutically active ingredients.

Examples of nutraceuticals include, but are not limited to, amino acids, terpenoids (e.g., carotenoid terpenoids and non-carotenoid terpenoids), herbal supplements, homeopathic supplements, glandular supplements, polyphenolics, flavonoid polyphenolics, phenolic acids, curcumin, resveratrol, lignans, glucosinolates, isothiocyanates, indoles, thiosulfinates, phytosterols, anthraquinones, capsaicin, piperine, chlorophyll, betaine, oxalic acid, acetyl-L-carnitine, allantoin, androstenediol, androstendione, betaine (trimethylglycine), caffeine, calcium pyruvate (pyruvic acid), carnitine, carnosine, carotene, carotenoid, choline, chlorogenic acid, cholic acid, chondroitin sulfate, chondroitin sulfate, cholestan, chrysin, coenzyme Q10, conjugated linoleic acid, corosolic acid, creatine, dehydroepiandrosterone, dichlorophen, diindolymethane, dimethylglycine, dimercapto succinic acid, ebselen, ellagic acid, enzymes, fisetin, formononetin, glucaric acid (glucarate), glucosamine (HCl or sulfate), glucosamine (N-acetyl), glutathione, hesperidine, hydroxy-3-methylbutyric acid, 5-hydroxytryptophan, indole-3-carbinol, inositol, isothiocyanates, linolenic acid-gamma, lipoic acid (alpha), melatonin, methylsulfonylmethane, minerals, naringin, pancreatin, para-aminobenzoic acid, paraben (methyl or propyl), phenolics, phosphatidylcholine, phosphatidylserine, phospholipids, phytosterols, progesterone, pregnenolone, omega-3 fatty acids, quercetin, resveratrol, D-ribose, rutin, S-adenosylmethionine, salicylic acid, sulforaphane, tartaric acid, taxifolin, tetrahydropalmatine, theophyline, theobromine, tigogenin, troxerutin, tryptophan, tocotrienol (alpha, beta, and gamma), zeaxanthin, gingko biloba, ginger, cat's claw, hypericum, aloe vera, evening primrose, garlic, capsicum, dong quai, ginseng, feverfew, fenugreek, echinacea, green tea, marshmallow, saw palmetto, tea tree oil, fish oil, psyllium, kava-kava, licorice root, mahonia aquifolium, hawthorne, yohimbe, tumeric, witch Hazel, valerian, mistletoe, bilberry, bee pollen, peppermint oil, beta-carotene, genistein, lutein, lycopene, the polyphenols, and the like. Further examples of suitable nutraceuticals include those listed in *Handbook of Nutraceuticals and Functional Foods*, Robert E. C. Wildman, Ed., CRC Press (2001), which is incorporated by reference herein for the teachings related to nutraceuticals.

Examples of non-steroidal anti-inflammatory drugs (NSAID) comprise aceclofenac, acemetacin, aloxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, fumarate esters, ibuprofen, indometacin, ketoprofen, ketorolac, lornoxicam, loxoprofen, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, tolmetin, or valdecoxib.

Other useful pharmaceutical ingredients or nutraceuticals that can be included as an active ingredient include fish oils, egg oils, squid oils, krill oils, nut oils, seed oils; soy oils, avocado oils, seabuckthorn seed or berry oils, clary sage seed oils, algal oils, flaxseed oils, sacha ichi oils, echium oils, hemp oils, omega-3 fatty acids, polyunsaturated omega-3 fatty acids, hexadecatrienoic acid (HTA), alpha-linolenic acid (ALA), stearidonic acid (SDA), eicosatrienoic acid (ETE), eicosatetraenoic acid (ETA), eicosapentaenoic acid (EPA, timnodonic acid), heneicosapentaenoic acid (HPA), docosapentaenoic acid (DPA), clupanodonic acid), docosahexaenoic acid (DHA, cervonic acid), tetracosapentaenoic acid, tetracosahexaenoic acid (nisinic acid), and free acids, etheyl esters, or other esters or salts thereof. In one aspect, the pharmaceutical ingredient is a highly purified omega-3 fatty acid, ester, or salt thereof.

Vitamins are nutraceuticals or pharmaceutical ingredients that include organic substances that are typically considered essential for the normal growth and activity of a subject (e.g., a human or non-human animal patient to whom the composition is to be administered). Examples of vitamins include, but are not limited to vitamin A (retinol), B1 (thiamine), B2 (riboflavin), B complex, B6 (pyridoxine), B12 (cobalamin), C (ascorbic acid), D (cholecalciferol), E (tocopherol), F (linoleic acid), G, H (biotin), and K, and choline, folic acid, inositol, niacin, pantothenic acid, and para-aminobenzoic acid.

Vitamins can also include naturally occurring inorganic substances that are typically considered essential for the normal growth and activity of a subject (e.g., a human or non-human animal patient to whom the composition is to be administered). Examples of minerals include, but are not limited to, boron, calcium, chromium, copper, iron, magnesium, manganese, molybdenum, nickel, phosphorus, selenium, silicon, tin, vanadium, and zinc.

In another embodiment, active drug substances suitable for use in the pharmaceutical compositions provided herein include: oxycodone, morphine, morphine analogues, or morphine antagonists, codeine, morphine, methadone, fentanyl and analogs, opioid pain relievers: oxycodone hydrochloride, hydrocodone bitartrate hydromorphone, oxymorphone, meperidine, propoxyphene, flunitrazepam, barbiturates, amytal, nembutal, seconal, phenobarbital; benzodiazepines, zolpidem, zaleplon, eszopiclone, amphetamines, or methylphenidate.

Examples of active drug substances suitable for use in the pharmaceutical compositions provided herein include: anti-inflammatory and antirheumatic active drug substances, such as, for example: butylpyrazolidine, phenylbutazone, mofebutazone, oxyphenbutazone, clofezone, kebuzone, acetic acid derivatives and related substances, indometacin, sulindac, tolmetin, zomepirac, diclofenac, alclofenac, bumadizone, etodolac, lonazolac, fentiazac, acemetacin, difenpiramide, oxametacin, proglumetacin, ketorolac, aceclofenac, bufexamac, oxicam, piroxicam, tenoxicam, droxicam, lornoxicam, meloxicam, methotrexate, fumarate esters, propionic acid derivatives, ibuprofen, naproxen, ketoprofen, fenoprofen, fenbufen, benoxaprofen, suprofen, pirprofen, flurbiprofen, indoprofen, tiaprofenic acid, oxaprozin, ibuproxam, dexibuprofen, flunoxaprofen, alminoprofen, dexketoprofen, fenamates, mefenamic acid, tolfenamic acid, flufenamic acid, meclofenamic acid, coxibs, celecoxib, rofecoxib, valdecoxib, parecoxib, etoricoxib, lumiracoxib, nabumetone, niflumic acid, azapropazone, glucosamine, benzydamine, glucosaminoglycan polysulfate, proquazone, orgotein, nimesulide, feprazone, diacerein, morniflumate, tenidap, oxaceprol, chondroitin sulfate, feprazone, dipyrocetyl, acetylsalicylic acid, quinolines, oxycinchophen, gold preparations, sodium aurothiomalate, sodium aurotiosulfate, auranofin, aurothioglucose, aurotioprol, penicillamine or bucillamine.

In another embodiment, suitable active pharmaceutical ingredients can comprise analgesics, such as, for example: opioids, natural opium alkaloids, morphine, opium, hydromorphone, nicomorphine, oxycodone, dihydrocodeine, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics, such as, for example: rimazolium, glafenine, floctafenine, viminol, nefopam, flupirtine, or ziconotide.

In another embodiment, suitable active pharmaceutical ingredients can comprise anaesthetics, such as, for example: ethers, diethyl ether, vinyl ether, halogenated hydrocarbons, halothane, chloroform, methoxyflurane, enflurane, trichloroethylene, isoflurane, desflurane, sevoflurane, barbiturates, methohexital, hexobarbital, thiopental, narcobarbital, opioid anaesthetics, fentanyl, alfentanil, sufentanil, phenoperidine, anileridine, remifentanil, other general anaesthetics, such as, for example: droperidol, ketamine, propanidid, alfaxalone, etomidate, propofol, hydroxybutyric acid, nitrous oxide, esketamine, xenon, esters of aminobenzoic acid, metabutethamine, procaine, tetracaine, chloroprocaine, benzocaine, amides, bupivacaine, lidocaine, mepivacaine, prilocaine, butanilicaine, cinchocaine, etidocaine, articaine, ropivacaine, levobupivacaine, esters of benzoic acid, cocaine, other local anaesthetics, such as, for example: ethyl chloride, dyclonine, phenol, or capsaicin.

In another embodiment, suitable active pharmaceutical ingredients can comprise antimigraine active drug substances, such as, for example: ergot alkaloids, dihydroergotamine, ergotamine, methysergide, lisuride, corticosteroid derivatives, flumedroxone, selective serotonin (5HT1) agonists, sumatriptan, naratriptan, zolmitriptan, rizatriptan, almotriptan, eletriptan, frovatriptan, other antimigraine preparations, pizotifen, clonidine, iprazochrome, dimetotiazine, or oxetorone.

In another embodiment, suitable active pharmaceutical ingredients can comprise antiepileptic active drug substances, such as, for example: barbiturates and derivatives, methylphenobarbital, phenobarbital, primidone, barbexaclone, metharbital, hydantoin derivatives, ethotoin, phenytoin, amino(diphenylhydantoin) valeric acid, mephenytoin, fosphenytoin, oxazolidine derivatives, paramethadione, trimethadione, ethadione, succinimide derivatives, ethosuximide, phensuximide, mesuximide, benzodiazepine derivatives, clonazepam, carboxamide derivatives, carbamazepine, oxcarbazepine, rufinamide, fatty acid derivatives, valproic acid, valpromide, aminobutyric acid, vigabatrin, progabide, tiagabine, other antiepileptics, such as, for example: sultiame, phenacemide, lamotrigine, felbamate, topiramate, gabapentin, pheneturide, levetiracetam, zonisamide, pregabalin, stiripentol, lacosamide, or beclamide.

In another embodiment, suitable active pharmaceutical ingredients can comprise anticholinergic active drug substances, such as, for example: tertiary amines, trihexyphenidyl, biperiden, metixene, procyclidine, profenamine, dexetimide, phenglutarimide, mazaticol, bornaprine, tropatepine, ethers chemically close to antihistamines, etanautine, orphenadrine (chloride), ethers of tropine or tropine derivatives, benzatropine, or etybenzatropine.

In another embodiment, suitable active pharmaceutical ingredients can comprise dopaminergic active drug substances, such as, for example: dopa and dopa derivatives, levodopa, melevodopa, etilevodopa, adamantane derivatives, amantadine, dopamine agonists, bromocriptine, pergolide, dihydroergocryptine mesylate, ropinirole, pramipexole, cabergoline, apomorphine, piribedil, rotigotine, monoamine, oxidase B inhibitors, selegiline, rasagiline, other dopaminergic agents, such as, for example: tolcapone, entacapone, or budipine.

In another embodiment, suitable active pharmaceutical ingredients can comprise antipsychotic active drug substances, such as, for example: phenothiazines with aliphatic side-chain, chlorpromazine, levomepromazine, promazine, acepromazine, triflupromazine, cyamemazine, chlorproethazine, phenothiazines with piperazine structure, dixyrazine, fluphenazine, perphenazine, prochlorperazine, thiopropazate, trifluoperazine, acetophenazine, thioproperazine, butaperazine, perazine, phenothiazines with piperidine structure, periciazine, thioridazine, mesoridazine, pipotiazine, butyrophenone derivatives, haloperidol, trifluperidol, melperone, moperone, pipamperone, bromperidol, benperidol, droperidol, fluanisone, indole derivatives, oxypertine, molindone, sertindole, ziprasidone, thioxanthene derivatives, flupentixol, clopenthixol, chlorprothixene, tiotixene, zuclopenthixol, diphenylbutylpiperidine derivatives, fluspirilene, pimozide, penfluridol, diazepines, oxazepines, thiazepines, loxapine, clozapine, olanzapine, quetiapine, neuroleptics, tetrabenazine, benzamides, sulpiride, sultopride, tiapride, remoxipride, amisulpride, veralipride, levosulpiride, lithium, other antipsychotics, such as, for example prothipendyl, risperidone, clotiapine, mosapramine, zotepine, aripiprazole, or paliperidone.

In another embodiment, suitable active pharmaceutical ingredients can comprise anxiolytic active drug substances, such as, for example: benzodiazepine derivatives, diazepam, chlordiazepoxide, medazepam, oxazepam, potassium clorazepate, lorazepam, adinazolam, bromazepam, clobazam, ketazolam, prazepam, alprazolam, halazepam, pinazepam, camazepam, nordazepam, fludiazepam, ethyl loflazepate, etizolam, clotiazepam, cloxazolam, tofisopam, diphenylmethane derivatives, hydroxyzine, captodiame, carbamates, meprobamate, emylcamate, mebutamate, dibenzo-bicyclooctadiene derivatives, benzoctamine, azaspirodecanedione derivatives, buspirone, other anxiolytics, such as, for example: mephenoxalone, gedocarnil, or etifoxine.

In another embodiment, suitable active pharmaceutical ingredients can comprise hypnotic and sedative active drug substances, such as, for example: barbiturates, pentobarbital, amobarbital, butobarbital, barbital, aprobarbital, secobarbital, talbutal, vinylbital, vinbarbital, cyclobarbital, heptabarbital, reposal, methohexital, hexobarbital, thiopental, ethallobarbital, allobarbital, proxibarbal, aldehydes and derivatives, chloral hydrate, chloralodol, acetylglycinamide chloral hydrate, dichloralphenazone, paraldehyde, benzodiazepine emepronium derivatives, flurazepam, nitrazepam, flunitrazepam, estazolam, triazolam, lormetazepam, temazepam, midazolam, brotizolam, quazepam, loprazolam, doxefazepam, cinolazepam, piperidinedione derivatives, glutethimide, methyprylon, pyrithyldione, benzodiazepine related drugs, zopiclone, zolpidem, zaleplon, ramelteon, other hypnotics and sedatives, such as, for example: methaqualone, clomethiazole, bromisoval, carbromal, scopolamine, propiomazine, triclofos, ethchlorvynol, valerian, hexapropymate, bromides, apronal, valnoctamide, methylpentynol, niaprazine, melatonin, dexmedetomidine, or dipiperonylaminoethanol.

In another embodiment, suitable active pharmaceutical ingredients can comprise antidepressant active drug substances, such as, for example: non-selective monoamine reuptake inhibitors, desipramine, imipramine, imipramine oxide, clomipramine, opipramol, trimipramine, lofepramine, dibenzepin, amitriptyline, nortriptyline, protriptyline, doxepin, iprindole, melitracen, butriptyline, dosulepin, amoxapine, dimetacrine, aminepetine, maprotiline, quinupramine, selective serotonin reuptake inhibitors, zimeldine, fluoxetine, citalopram, paroxetine, sertraline, alaproclate, fluvoxamine, etoperidone, escitalopram, monoamine oxidase inhibitors, isocarboxazid, nialamide, phenelzine, tranylcypromine, iproniazide, iproclozide, monoamine oxidase A inhibitors, moclobemide, toloxatone, other antidepressants, such as, for example: oxitriptan, tryptophan, mianserin, nomifensine, trazodone, nefazodone, minaprine, bifemelane, viloxazine, oxaflozane, mirtazapine, medifoxamine, tianeptine, pivagabine, venlafaxine, milnacipran, reboxetine, gepirone, duloxetine, agomelatine, desvenlafaxine, centrally acting sympathomimetics, such as, for example: amfetamine, dexamfetamine, lisdexamfetamine, metamfetamine, methylphenidate, dexmethylphenidate, pemoline, fencamfamin, modafinil, fenozolone, atomoxetine, fenetylline, xanthine derivatives, caffeine, propentofylline, other psychostimulants and nootropics, such as, for example meclofenoxate, pyritinol, piracetam, deanol, fipexide, citicoline, oxiracetam, pirisudanol, linopirdine, nizofenone, aniracetam, acetylcarnitine, idebenone, prolintane, pipradrol, pramiracetam, adrafinil, or vinpocetine.

In another embodiment, suitable active pharmaceutical ingredients can comprise anti-dementia active drug substances, such as, for example: anticholinesterases, tacrine, donepezil, rivastigmine, galantamine, other anti-dementia drugs, memantine, or ginkgo biloba.

In another embodiment, suitable active pharmaceutical ingredients can comprise other nervous system active drug substances, such as, for example: parasympathomimetics, anticholinesterases, neostigmine, pyridostigmine, distigmine, ambenonium, choline esters, carbachol, bethanechol, other parasympathomimetics, such as, for example: pilocarpine, or choline alfoscerate.

Active drug substances used in addictive disorders, such as, for example: nicotine, bupropion, varenicline, disulfiram, calcium carbimide, acamprosate, naltrexone, buprenorphine, methadone, levacetylmethadol, lofexidine, betahistine, cinnarizine, flunarizine, acetylleucine, gangliosides and ganglioside derivatives, tirilazad, riluzole, xaliproden, hydroxybutyric acid, or amifampridine.

In another embodiment, suitable active pharmaceutical ingredients can comprise opium alkaloids and derivatives, such as, for example: ethylmorphine, hydrocodone, codeine, opium alkaloids with morphine, normethadone, noscapine, pholcodine, dextromethorphan, thebacon, dimemorfan, acetyldihydrocodeine, benzonatate, benproperine, clobutinol, isoaminile, pentoxyverine, oxolamine, oxeladin, clofedanol, pipazetate, bibenzonium bromide, butamirate, fedrilate, zipeprol, dibunate, droxypropine, prenoxdiazine, dropropizine, cloperastine, meprotixol, piperidione, tipepidine, morclofone, nepinalone, levodropropizine, or dimethoxanate.

In another embodiment, the active pharmaceutical ingredient may be a substance with abuse potential that presents a safety risk. Such active drug substance may include: 1-(1-phenylcyclohexyl)pyrrolidine, 1-(2-phenylethyl)-4-phenyl-4-acetoxypiperidine, 1-[1-(2-thienyl)-cyclohexylpiperidine, 1-[1-(2-thienyl)cyclohexyl]pyrrolidine, 1-methyl-4-phenyl-4-propionoxy-piperidine,
1-phenylcyclohexylamine, 1-piperidinocyclohexanecarbonitrile, 2,5-dimethoxy-4-ethylamphetamine, 2,5-dimethoxyamphetamine, 2C-B-(4-bromo-2,5-dimethoxypenethylamine), 2C-D (2,5-dimethoxy-4-methylphenethylamine), 2C-I (4-iodo-2,5-dimethoxy-phenethylamine), 2C-T-2 (2,5-dimethoxy-4-ethylthiophenethylamine), 2C-T-4 (2,5-dimethoxy-4-isopropyl thiophenethylamine), 2C-T-7 (2,5-dimethoxy-4-(n)-propylthiophenethylamine), 3,4-methylenedioxymethamphetamine, 3,4,5-trimethoxyamphetamine, 3,4-methylenedioxyamphetamine, 3,4-methylenedioxy-N-ethylamphetamine, 3-methylfentanyl, 3-methylthiofentanyl, 4-bromo-2,5-dimethoxyamphetamine, 4-bromo-2,5-dimethoxyphenethylamine, 4-methoxyamphetamine, 4-methyl-2,5-dimethoxyamphetamine, 4-methylaminorex (cis isomer), 5-MeO-DIPT (5-methoxy-N,N-diisopropyltryptamine), 5-MeO-DMT (5-methoxy-N,N-dimethyltryptamine), 5-methoxy-3,4-methylenedioxyamphetamine, acetorphine, acetorphine, acetyl-alpha-methylfentanyl, acetyl-alpha-methylfentanyl, acetyldihydrocodeine, acetylmethadol, acetylmethadol, alfentanil, allobarbital, allylprodine, alphacetylmethadol except levo-alphacetylmethadol, alpha-ethyltryptamine, alphameprodine, alphamethadol, alphamethadol, alpha-methylfentanyl, alpha-methylthiofentanyl, alphaprodine, alprazolam, amfepramon, amfetaminil, amineptin, aminorex, amobarbital, amphetamine, dextroamphetamine, amilnitrite (all isomers of the amyl group), anabolic steroids, anileridine, aprobarbital, barbital, barbituric acid derivative, BDB (3,4-methylenedioxyphenyl)-2-butanamine), benzethidin, benzethidine, benzoylecgonine, benzphetamine, benzphetamine, benzylmethylcetone, benzylmorphine, betacetylmethadol, beta-hydroxy-3-methylfentanyl, beta-hydroxyfentanyl, betameprodine, betameprodine, betamethadol, betaprodine, bezitramide, bezitramide, boldenone, brolamfetamine, bromazepam, brotizolam, bufotenine, buprenorphine, butabarbital, butalbital, butobarbital, butorphanol, BZP (A 2)(1-benzylpiperazin), camazepam, cannabis, carfentanil, catha edulis, cathine, cathinone, chloral betaine, chloral hydrate, chlordiazepoxide, chlorhexadol, chlorotestosterone (same as clostebol), chlorphentermine, clobazam, clonazepam, clonitazene, clonitazene, clorazepate, clortermine, clostebol, clotiazepam, cloxazolam, coca leaves, cocaine, codeine, codeine and isoquinoline alkaloid, codeine methylbromide, codeine-N-oxide, codoxime, cyclobarbital (hexemal NFN), cyprenorphine, dehydrochlormethyltestosterone, delorazepam, desomorphine, dexamfetamine, dexfenfluramine, dexmethylphenidate, dextromoramide, dextropropoxyphene, diacetylmorphine, diampromide, diazepam, dichloralphenazone, diethylpropion, diethylthiambutene, diethyltryptamine, difenoxin, dihydrocodeine, dihydroetorphine, dihydromorphine, dihydrotestosterone, dimenoxadol, dimepheptanol, dimethylthiambutene, dimethyltryptamine, dioxaphetyl butyrate, diphenoxylate, dipipanone, diprenorphine, dronabinol, drostanolone, drotebanol, ecgonine, estazolam, ethchlorvynol, ethinamate, ethyl loflazepate, ethylestrenol, ethylmethylthiambutene, ethylmorphine, ethylmorphine, eticyclidine, etilamfetamine, etonitazene, etorphine, etoxeridine, etryptamine, fencamfamin, fenethylline, fenetylline, fenfluramine, fenproporex, fentanyl, fludiazepam, flunitrazepam, fluoxymesterone, flurazepam, formebolone, fungi and spores of the species psilocybe semilanceata, furethidine, gamma hydroxybutanoic acid, glutethimide, halazepam, haloxazolam, heroine, hydrocodone, hydrocodone & isoquinoline alkaloid, hydromorphinol, hydromorphone, hydroxypethidine, ibogaine, isobutylnitrite, isomethadone, ketamine, ketazolam, ketobemidone, levamfetamine, levo-alphacetylmethadol, levo-methamphetamine, levomethorphan, levomoramide, levophenacylmorphan, levorphanol, lisdexamfetamine, loprazolam, lorazepam, lormetazepam, lysergic acid, lysergic acid amide, lysergic acid diethylamide, marijuana, mazindol, MBDN (N-methyl-1-(3,4-methylenedioxyphenyl)-2-butanamine), mCPP (1-(3-chlorphenyl)piperazine), mebutamate, mecloqualone, medazepam, mefenorex, MeOPP (1-(4-methoxyphenyl)piperazine), meperidine, meperidine intermediate, meprobamate, mescaline, mesocarb, mesterolone, metamfetamine, metazocine, methadone, methadone intermediate, methamphetamine, methandienone, methandrolone, methandriol, methandrostenolone, methaqualone, methcathinone, methenolone, methohexital, methyldesorphine, methyldihydromorphine, methylphenidate, methylphenobarbital (mephobarbital), methyltestosterone, methyprylone, metopone, mibolerone, midazolam, modafinil, moramide-intermediate, morpheridine, morphine, morphine methylbromide, morphine methylsulfonate, morphine-N-oxide, myrophine, N,N-dimethylamphetamine, nabilone, nalorphine, nandrolone, N-ethyl-1-phenylcyclohexylamine, N-ethyl-3-piperidyl benzilate, N-ethylamphetamine, N-hydroxy-3,4-methylenedioxyamphetamine, nicocodeine, nicocodine, nicodicodine, nicomorphine, nimetazepam, nitrazepam, N-methyl-3-piperidyl benzilate, noracymethadol, norcodeine, nordiazepam, norethandrolone, norlevorphanol, normethadone, normorphine, norpipanone, norpipanone, opium, oxandrolone, oxazepam, oxazolam, oxycodone, oxymesterone, oxymetholone, oxymorphone, para-fluorofentanyl, parahexyl, paraldehyde, pemoline, pentazocine, pentobarbital, petrichloral, peyote, phenadoxone, phenampromide, phenazocine, phencyclidine, phendimetrazine, phenmetrazine, phenobarbital, phenomorphan, phenoperidine, phentermine, phenylacetone, pholcodine, piminodine, pinazepam, pipradrole, piritramide, PMMA (paramethyxymethyl amphetamine), prazepam, proheptazine, properidine, propiram, psilocybine, psilocine, pyrovalerone, quazepam, racemethorphane, racemoramide, racemorphane, remifentanil, salvia divinorum, salvinorin A, secobarbital, secobarbital, sibutramine, SPA, stanolone, stanozolol, sufentanil, sulfondiethylmethane, sulfonethylmethane, sulfonmethane, talbutal, temazepam, tenamfetamine, testolactone, testosterone, tetrahydrocannabinols, tetrazepam, TFMPP (1-(3-triflourmethylphenyl)piperazine), thebacon, thebaine, thiamylal, thiofentanyl, thiopental, tiletamine and zolazepam in combination, tilidine, trenbolone, triazolam, trimeperidine, vinbarbital, zaleplon, zipeprol, zolpidem, or zopiclone.

Other suitable examples of active drug substances suitable for use in the pharmaceutical compositions described herein include, for example, alfentanil, allylprodine, alphaprodine, anileridine, benzylmorphine, bezitramide, buprenorphine, butorphanol, clonitazene, codeine, cyclazocine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, dextropropoxyphene, ketobemidone, levallorphan, levorphanol, levophenacylmorphan, lofentanil, meperidine, meptazinol, metazocine, methadone, metopon, morphine, morphine 6-glucuronide, morphine 3-glucuronide, myrophine, nalbuphine, narceine, nicomorphine, norlevorphanol, normethadone, nalorphine, normorphine, norpipanone, opium, oxycodone, oxycodeine, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, thebaine, levo-alphacetylmethadol (LAAM), remifentanil, carfentanyl, ohmefentanyl, MPPP, prodine, PEPAP, levomethorphan, etorphine, lefetamine, loperamide, diphenoxylate, or pethidine.

Other examples of active drug substances suitable for use in the pharmaceutical compositions described herein include anabolic steroids, cannabis, cocaine, or diazepam.

In another embodiment, the active drug substance comprises the therapeutic classes including non-steroidal anti-inflammatory substances or antirheumatic active drug substances.

In one embodiment, the active drug substance comprises analgesics, opioids, antipyretics, anaesthetics, antimigraine agents, antiepileptics, anti-parkinson agents, dopaminergic agents, antipsychotics, anxiolytics, sedatives, antidepressants, psychostimulants agents, dopamine, noradrenaline, nicotinic, alpha-adrenergic, serotonin, H3 antagonists used for ADHD or nootropics agents used in addictive disorders.

In one embodiment, the active drug substance comprises therapeutic classes including anaesthetics, centrally acting analgesics, sedative-hypnotics, anxiolytics, appetite suppressants, decongestants, antitussives, antihistamines, antiemetics, antidiarrheals, and drugs used to treat narcolepsy, or attention deficit hyperactivity disorder.

In another embodiment, the active drug substance is associated with abuse syndromes and the active drug substance may, for example, be selected from opioids, CNS depressants, CNS stimulants, cannabinoids, nicotine-like compounds, glutamate antagonists, or N-methyl-D-aspartate (NMDA) antagonists.

In another embodiment, the active drug substance is an analgesic. Examples of analgesics suitable for use in the pharmaceutical compositions described herein include, for example, opioids, natural opium alkaloids, morphine, opium, hydromorphone, nicomorphine, oxycodone, dihydrocodeine, diamorphine, tapentadol, papaveretum, codeine, phenylpiperidine derivatives, ketobemidone, pethidine, fentanyl, diphenylpropylamine derivatives, dextromoramide, piritramide, dextropropoxyphene, bezitramide, methadone, benzomorphan derivatives, pentazocine, phenazocine, oripavine derivatives, buprenorphine, morphinan derivatives, butorphanol, nalbuphine, tilidine, tramadol, dezocine, salicylic acid and derivatives, acetylsalicylic acid, aloxiprin, choline salicylate, sodium salicylate, salicylamide, salsalate, ethenzamide, morpholine salicylate, dipyrocetyl, benorilate, diflunisal, potassium salicylate, guacetisal, carbasalate calcium, imidazole salicylate, pyrazolones, phenazone, metamizole sodium, aminophenazone, propyphenazone, nifenazone, anilides, paracetamol, phenacetin, bucetin, propacetamol, other analgesics and antipyretics such as, for example, rimazolium, glafenine, floctafenine, viminol, nefopam, flupirtine, or ziconotide.

In another embodiment, the active drug substance is an opioid. Where an opioid is included as an active drug substance, the opioid may comprise naturally occurring opioids, synthetic opioids, or semisynthetic opioids.

In other embodiment, the active drug substance comprises amfetamine, dexamfetamine, lisdexamfetamine, metamfetamine, methylphenidate, dexmethylphenidate, or combinations thereof.

In another embodiment, the pharmaceutical compositions disclosed herein includes an opioid, the opioid is selected from buprenorphine, codeine, dextromoramide, dihydrocodeine, fentanyl, hydrocodone, hydromorphone, morphine, pentazocine, oxycodeine, oxycodone, oxymorphone, norhydrocodone, noroxycodone, morphine-6-glucuronode, tramadol, tapentadol, or dihydromorphine.

Where an opioid is used as an active drug substance, the opioid may be present in any of its crystalline, polymorphous, semi-crystalline, and amorphous or polyamorphous forms. Furthermore, in another embodiment, an opioid used as an active drug substance may be present in one or more forms selected from its crystalline, polymorphous, semi-crystalline, or amorphous or polyamorphous forms.

Another embodiment of the pharmaceutical compositions disclosed herein include an opioid as an active drug substance, the active drug substance is selected from morphine, oxycodone, hydrocodone, hydromorphone, norhydrocodone, oxymorphone, noroxycodone, morphine-6-glucuronode and pharmaceutically acceptable salts thereof, including oxycodone hydrochloride, hydrocodone bitartrate, hydromorphone hydrochloride or morphine sulphate pentahydrate.

In one embodiment, the pharmaceutical compositions as described herein are suitable for use for water soluble as well as slightly soluble or insoluble active drug substances.

In another embodiment, all of the above mentioned active drug substances may also be in the form of pharmaceutically acceptable salts, uncharged or charged molecules, molecular complexes, solvates, or anhydrates thereof, and, if relevant, single isomers, enantiomers, racemic mixtures, or mixtures thereof.

In another embodiment, the pharmaceutical compositions described herein may comprise pharmaceutically acceptable salts of any of the above mentioned active drug substances.

One embodiment described herein is a pharmaceutical composition comprising an enteric soft capsule as described herein comprising an active pharmaceutical ingredient or plurality of active pharmaceutical ingredients.

Another embodiment described herein is a method for treating, ameliorating the symptoms of, or delaying the onset of a medical condition by providing a subject in need thereof with a pharmaceutical composition comprising an enteric soft capsule, as described herein, comprising a pharmaceutical ingredient or ingredients. As used herein, a medical condition can comprise any actual or suspected disease, disorder, or condition that a subject may seek medical care therefor. One embodiment described herein is method of treating, ameliorating the symptoms of, or delaying the onset of a medical condition of includes administering a pharmaceutical ingredient having a desired therapeutic or biological activity or suspected of having a desired therapeutic or biological activity in a subject in need thereof.

In one embodiment described herein, the ratio of the active ingredient or drug to the total matrix fill (e.g., matrix fill ingredient(s) and active pharmaceutical ingredient(s)) can be from about 1:50 to about 1:1 by weight, including all ratios in the specified range. In another embodiment described herein, the active ingredient to total matrix fill ratio can also be from about 1:16 to about 1:1 by weight, including all ratios in the specified range. The active ingredient to total matrix fill ratio can also be about 1:16; about 1:9; about 1:3; about 1:2; or about 1:1 including all ratios in the specified range.

In one embodiment described herein, the active ingredient or drug comprises from about 5% to about 80% of the matrix fill mass including all iterations of integers within the specified range. In one aspect described herein, the active ingredient or drug comprises about 80% of the matrix fill mass. In another aspect, the active ingredient or drug comprises about 60% of the matrix fill mass. In another aspect, the active ingredient or drug comprises about 40% of the matrix fill mass. In another aspect, the active ingredient or drug comprises about 6% of the matrix fill mass. In another embodiment described herein, the active ingredient or drug comprises about 80%, about 70%, about 60%, about 50%, about 40%, about 30%, about 20%; about 15%; about 10%; about 5%; about 2%, or about 1% of the matrix fill mass.

In one embodiment, the pharmaceutical composition described herein, comprises an active pharmaceutical ingredient of about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, or even more.

In another embodiment, the pharmaceutical composition described herein, comprises an active pharmaceutical ingredient in the range of about 20 mg to about 250 mg, about 30 mg to about 250 mg, about 40 mg to about 250 mg, about 50 mg to about 250 mg, about 60 mg to about 250 mg, about 70 mg to about 250 mg, about 80 mg to about 250 mg, about 90 mg to about 250 mg, about 100 mg to about 250 mg, about 110 mg to about 250 mg, about 120 mg to about 250 mg, about 130 mg to about 250 mg, about 140 mg to about 250 mg, about 150 mg to about 250 mg, about 160 mg to about 250 mg, about 170 mg to about 250 mg, about 180 mg to about 250 mg, about 190 mg to about 250 mg, about 200 mg to about 250 mg, about 210 mg to about 250 mg, about 220 mg to about 250 mg, about 230 mg to about 250 mg, or about 240 mg to about 250 mg including all iterations of integers within the specified ranges above.

The dosage form can be administered, for example, 1×, 2×, 3×, 4×, 5×, 6×, 7×, or 8×, per day. One or more dosage form can be administered, for example, for 1, 2, 3, 4, 5, 6, 7 days, or even longer. One or more dosage forms can be administered, for example, for 1, 2, 3, 4 weeks, or even longer. One or more dosage forms can be administered, for example, for 1, 2, 3, 4, 5, 6, 7, 8, 9, 10, 11, 12 months, or even longer. One or more dosage forms can be administered until the patient, subject, mammal, mammal in need thereof, human, or human in need thereof, does not require treatment, prophylaxis, or amelioration of any disease or condition such as, for example, pain.

In another embodiment described herein, the total mass of the matrix fill of the pharmaceutical composition described herein that comprises an active pharmaceutical ingredient described herein is from about 50 mg to about 500 mg. In one aspect, the total mass of the matrix fill mass is about 80 mg. In one aspect, the total mass of the matrix fill mass is about 220 mg. In one aspect, the total mass of the matrix fill mass is about 420 mg. In one aspect, the total mass of the matrix fill mass is about 220 mg. In one aspect, the total mass of the matrix fill mass is about 500 mg.

In one embodiment described herein, the weight ratio range of the active pharmaceutical ingredient to the matrix fill mass is about 1:20 to about 10:1. In one aspect, the weight ratio of the active pharmaceutical ingredient to the matrix fill mass is about 1:3. In one aspect, the weight ratio of the active pharmaceutical ingredient to the matrix fill mass is about 1:9. In one aspect, the weight ratio of the active pharmaceutical ingredient to the matrix fill mass is about 1:17.

In one embodiment described herein, the enteric soft gelatin shell and matrix fills described herein prevent or reduce the onset of esophageal irritation, esophageal erosion, gastric irritation, gastric reflux, peptic ulcers, stomach bleeding or ulceration from non-steroidal anti-inflammatory drug administration. In one aspect, the enteric soft gelatin shell and matrix fills described herein prevent or reduce the onset of esophageal irritation, esophageal erosion, gastric irritation, gastric reflux, peptic ulcers, stomach bleeding or ulceration from diclofenac administration. Without being bound to any theory, it is believed that the enteric soft gelatin capsule shells are able to prevent or reduce the onset of esophageal irritation, esophageal erosion, gastric irritation, gastric reflux, peptic ulcers by being easily and quickly swallowed and also by restricting the release of the non-steroidal anti-inflammatory drug after ingestion to the intestine. Without controlled release in the intestine, non-steroidal anti-inflammatory drugs inhibit prostaglandin synthesis locally in the stomach, which increases stomach acidity that leads to esophageal damage and stomach ulceration.

The liquid active ingredients can be prepared to contain the active pharmaceutical ingredient in the range of about 0.005% to about 100%, including all iterations of integers with the specified range, with the balance made up from non-toxic carrier. Methods for preparation of these compositions are known to those skilled in the art. See, for example, Remington's Pharmaceutical Sciences, Mack Publishing Company, Easton, Pa., 15$^{th}$ Edition, 1975. The liquid portion of the matrix fill can contain about 0.001% to about 100%, about 0.1% to about 95%, about 1% to about 90%, about 5% to about 70%, or about 10% to about 50% by weight of active ingredient.

In one embodiment described herein, the soft capsules described herein comprises a matrix fill having controlled, delayed, or extended release properties. Such controlled or extended release matrix fills are described in International Patent Application Publication No. WO 2005/009409 and U.S. Patent Application Publication No. US 2006/0115527, both of which are incorporated by reference herein for such teachings. In one aspect, the matrix fill can be configured to provide controlled release, extended release, sustained release, delayed release, or combinations thereof.

Accordingly, one embodiment described herein is a controlled release enteric soft capsule having a shell and a matrix fill, wherein the matrix fill includes an active pharmaceutical ingredient.

In one embodiment, the active pharmaceutical ingredient can be dispersed or suspended in the liquid carrier. In another embodiment, the active ingredient can be prepared in a self-emulsifying/microemulsifying drug delivery system (SEDDS/SMEDDS). Optionally, the SEDDS system can include an oil, a surfactant, a cosurfactant or solubilizer, and the active ingredient.

It will be readily apparent to one of ordinary skill in the relevant arts that suitable modifications and adaptations to the compositions, methods, and applications described herein can be made without departing from the scope of any embodiments or aspects thereof. The compositions and methods provided are exemplary and are not intended to limit the scope of the claimed embodiments. All of the various aspects, embodiments, and options disclosed herein can be combined in all variations. The scope of the compositions and methods described herein include all actual or potential combinations of embodiments, aspects, examples, and preferences herein described. All patents and publications cited herein are entirely incorporated by reference herein for the specific teachings thereof.

EXAMPLES

Example 1

Examples of gel mass compositions useful for producing gelatin enteric soft capsules are shown below in Table 6. Composition components are set forth by weight percentage of the total weight of the gel mass composition.

TABLE 6

Exemplary Enteric Soft Capsule Gel Masses

| Ingredient | Weight Percentage (%) | | | | | |
|---|---|---|---|---|---|---|
| | EX 1 | EX 2 | EX 3 | EX 4 | EX 5 | EX 6 |
| Poly(methacylic acid-co-ethyl acrylate) 1:1 (enteric A) | 5 | 11 | 10.5 | 12 | 2.25 | 6.64 |
| Poly(ethyl acrylate-co-methyl methacrylate) 2:1 (enteric B) | 0 | 0 | 0 | 0 | 0 | 0 |
| Poly(methyl acrylate-co-methyl methacrylate-co-methacrylic acid) 7:3:1 (enteric C) | 0 | 0 | 0 | 0 | 12.75 | 1.36 |
| Neutralizer | 3 | 3.5 | 3.57 | 0 | 3.5 | 2.72 |
| Plasticizer | 10.5 | 17.8 | 22 | 15.2 | 22.75 | 19 |
| Type B gelatin | 25 | 27.8 | 0 | 28 | 9 | 0 |
| Type A gelatin, 175 Bloom | 0 | 0 | 35 | 7 | 0 | 18 |
| Type A gelatin, 195 Bloom | 0 | 0 | 0 | 0 | 27.0 | 0 |
| Solvent | 46 | 22.1 | 6.93 | 22.6 | 0 | 33.28 |
| TOTAL | 100 | 100 | 100 | 100 | 100 | 100 |
| Components and Relational Ratios | | | | | | |
| Total enteric polymer | 5 | 10.8 | 10.5 | 12 | 15 | 8 |
| Total gelatin | 25 | 27.8 | 35 | 35 | 36 | 18 |
| Total polymer (total enteric + gelatin) | 30 | 38.8 | 45.5 | 47 | 51 | 26 |
| Ratio gelatin to total enteric | 5.00 | 2.57 | 3.33 | 2.92 | 2.40 | 2.25 |
| Ratio gelatin to plasticizer | 2.38 | 1.56 | 1.59 | 2.30 | 1.58 | 0.95 |
| Ratio plasticizer to total polymer | 0.35 | 0.46 | 0.48 | 0.32 | 0.45 | 0.73 |
| Ratio plasticizer to total enteric | 2.10 | 1.62 | 2.10 | 1.27 | 1.52 | 2.38 |
| Ratio neutralizer to total enteric | 0.60 | 0.32 | 0.34 | — | 0.23 | 0.34 |
| Ratio enteric A to total enteric polymer | 1.00 | 1.02 | 1.00 | 1.00 | 0.15 | 0.83 |
| Ratio enteric B to total enteric polymer | — | — | — | — | 0.85 | 0.17 |
| Ratio enteric C to total enteric polymer | — | — | — | — | — | — |

Example 2

Examples of gel mass compositions useful for producing gelatin enteric soft capsules are shown below in Table 7. Composition components are set forth by weight percentage of the total weight of the gel mass composition.

TABLE 7

Exemplary Enteric Soft Capsule Gel Masses Cont.

| Ingredient | Weight Percentage (%) | | | | | |
| --- | --- | --- | --- | --- | --- | --- |
|  | EX 7 | EX 8 | EX 9 | EX 10 | EX 11 | EX 12 |
| Poly(methacylic acid-co-ethyl acrylate) 1:1 (enteric A) | 5.5 | 4.5 | 11 | 12 | 13 | 9 |
| Poly(ethyl acrylate-co-methyl methacrylate) 2:1 (enteric B) | 4.04 | 0 | 0.25 | 4 | 2.25 | 0.85 |
| Poly(methyl acrylate-co-methyl methacrylate-co-methacrylic acid) 7:3:1 (Enteric C) | 8.46 | 10.5 | 0 | 0 | 0 | 0 |
| Neutralizer | 1.3 | 0 | 6.8 | 2.5 | 1.9 | 0 |
| Plasticizer | 25 | 13.5 | 14 | 16.5 | 23.7 | 15.8 |
| Type B gelatin | 28 | 0 | 28 | 0 | 0 | 35 |
| Type A gelatin, 175 Bloom | 0 | 0 | 0 | 29 | 0 | 0 |
| Type A gelatin, 195 Bloom | 0 | 35 | 7 | 0 | 27.8 | 0 |
| Solvent | 2.7 | 23 | 18.95 | 19.5 | 7.65 | 23.55 |
| TOTAL | 100 | 100 | 100 | 100 | 100 | 100 |
| Components and Relational Ratios | | | | | | |
| Total enteric polymer | 18.00 | 15.00 | 11.25 | 16.00 | 15.25 | 9.85 |
| Total gelatin | 28.00 | 35.00 | 35.00 | 29.00 | 27.80 | 35.00 |
| Total polymer (total enteric + gelatin) | 46.00 | 50.00 | 46.25 | 45.00 | 43.05 | 44.85 |
| Ratio gelatin to total enteric | 1.56 | 2.33 | 3.11 | 1.81 | 1.82 | 3.55 |
| Ratio gelatin to plasticizer | 1.12 | 2.59 | 2.50 | 1.76 | 1.17 | 2.22 |
| Ratio plasticizer to total polymer | 0.54 | 0.27 | 0.30 | 0.37 | 0.55 | 0.35 |
| Ratio plasticizer to total enteric | 1.39 | 0.90 | 1.24 | 1.03 | 1.55 | 1.60 |
| Ratio neutralizer to total enteric | 0.07 | 0.00 | 0.60 | 0.16 | 0.12 | 0.00 |
| Ratio enteric A to total enteric polymer | 0.31 | 0.30 | 0.98 | 0.75 | 0.85 | 0.91 |
| Ratio enteric B to total enteric polymer | 0.47 | 0.70 | — | — | — | — |
| Ratio enteric C to total enteric polymer | 0.22 | — | 0.02 | 0.25 | 0.15 | 0.09 |

Example 3

Enteric soft capsules as described herein were prepared using the composition shown in Table 8.

TABLE 8

Exemplary Enteric Soft Capsule Gel Masses

| Ingredient | Weight Percentage (%) | | | | | |
| --- | --- | --- | --- | --- | --- | --- |
|  | EX 1 | EX 2 | EX 3 | EX 4 | EX 5 | EX 6 |
| EUDRAGIT ® L100-55 | 7.6 | 11 | 11 | 7.6 | 11 | 10.3 |
| EUDRAGIT ® NE 40D | 0 | 0 | 0.23 | 0 | 0 | 0.2 |
| EUDRAGIT ® FS30D | 3.2 | 0 | 0 | 3.2 | 0 | 0 |
| 1N NaOH | 2.5 | 3.7 | 3.7 | 2.5 | 3.7 | 3.4 |
| Glycerol | 17.8 | 17.8 | 18.4 | 17.8 | 18.3 | 17.8 |
| Lime bone gelatin, 150 Bloom | 27.8 | 0 | 0 | 28.8 | 0 | 0 |
| Pig skin gelatin, 175 Bloom | 0 | 27.8 | 27.8 | 0 | 0 | 27.8 |
| Acid bone gelatin, 195 Bloom | 0 | 0 | 0 | 0 | 27.8 | 0 |
| Water | 41 | 39.7 | 38.8 | 40 | 39.2 | 40.5 |
| TOTAL | 100 | 100 | 100 | 100 | 100 | 100 |

Example 4

Enteric soft capsules as described herein were prepared using the composition shown in Table 9.

TABLE 9

Exemplary Enteric Soft Capsule Gel Mass

| Ingredient | Weight Percentage (%) | | |
| --- | --- | --- | --- |
|  | Formula 1 | Formula 2 | Formula 3 |
| EUDRAGIT ® L100-55 | 10.8 | 10.5 | 10.8 |
| 1N NaOH | 3.6 | 3.5 | 0 |
| Glycerol | 17.8 | 17.8 | 17.8 |
| Lime bone gelatin, 150 Bloom | 27.8 | 0 | 27.8 |
| Pig skin gelatin, 175 Bloom | 0 | 0 | 0 |
| Acid bone gelatin, 195 Bloom | 0 | 26.8 | 0 |
| Water | 40 | 41.4 | 43.6 |
| TOTAL | 100 | 100 | 100 |

Example 5

The enteric properties of the enteric soft capsule compositions listed in Table 9 were subsequently tested. The results of these tests are shown in Table 10. At least 12 capsules per batch formulation were tested. All of the capsules remained intact in the acidic stage (2 hrs 0.1 N HCl) and passed the basic buffer stage (1 hr buffer at pH 6.8). All of the formulations from Table 9 were tested at 1 week, 1 month, and 9 months after manufacturing and passed both the acid and basic buffer stages.

TABLE 10

Disintegration Results Utilizing Exemplary Enteric Soft Capsule Gel Masses

| Batch No. | Gel Composition | Fill Type | Fill Weight (mg) | Capsule Size | 2 hr 0.1N HCl | 1 hr pH 6.8 |
|---|---|---|---|---|---|---|
| 913-A | Formula 1 | Fish oil | 600 | 12 EXL oval | Pass | Pass |
| 913-B | Formula 1 | Fish oil | 1000 | 23 oblong | Pass | Pass |
| 2613-A | Formula 2 | Fish oil | 600 | 12EXL oval | Pass | Pass |
| 613-B | Formula 2 | Fish oil | 1000 | 23 oblong | Pass | Pass |
| 8A6 | Formula 1 | Fish oil | 500 | 12EXL oval | Pass | Rupture at 1:30 h |
| 8A3 | Formula 1 | Peppermint oil | 180 | 4E oval | Pass | Rupture at 1:30 h |
| 8A4 | Formula 1 | Valproic acid | 500 | 12EXL oval | Pass | Rupture at 1:15 h |
| 8A | Formula 3 | Fish Oil | 500 | 12EXL oval | Pass | Rupture at 1:15 h |
| 8A1 | Formula 3 | Valproic acid | 500 | 12EXL oval | Pass | Rupture at 1:30 h |
| 8A2 | Formula 3 | Peppermint oil | 180 | 4E oval | Pass | Rupture at 1:15 h |
| 1A7 | Formula 2 | Fish oil | 500 | 12EXL oval | Pass | Rupture at 1:15 h |

Example 6

Films of the enteric soft capsule compositions listed in Table 11 were subjected to European Pharmacopoeia disintegration testing for gastro resistant formulas (e.g., EP 2.9.1). Both compositions passed the acid (0.1 N HCl) and buffer (phosphate buffer, pH 6.8) stages of the test.

TABLE 11

Enteric Composition with Eudragit L30D-55/Eudragit FS-30D-55 Ratio 7:3

| Component | RDT-080 Percent Weight (%) | RDT-081 Percent Weight (%) |
|---|---|---|
| Eudragit ® L30D-55 (30% dispersion)* | 25.2 | 26.37 |
| Eudragit ® FS-30D (30% dispersion)* | 10.8 | 11.3 |
| 1M NaOH Solution | 2.52 | 2.64 |
| Water | 15.88 | 14.09 |
| Glycerol | 17.80 | 17.80 |
| Lime Bone gelatin, 150 Bloom | — | — |
| Acid Bone gelatin, 195 Bloom | 27.8 | 27.80 |
| TOTAL | 100 | 100 |

*RDT-080: Total dry weight of enteric polymers (L30D-55 + FS-30D): 10.8%
*RDT-081: Total dry weight of enteric polymers(L30D-55 + FS-30D): 11.3%

Example 7

Enteric soft capsules comprising fills of valproic acid were manufactured and stored for approximately 1 year and then subjected to USP-NF (711) Method B (delayed release dosage form) using Apparatus 2 (Paddle Apparatus). The results are shown in Table 12. There was approximately 45% release during the 2-hour acid stage for 1 vessel for lot A1 and about 40% release during the 2-hour acid stage for lot A4. The release in the buffer stage was low for both lots. Without being bound to any theory, the age of the capsules may have affected the dissolution results.

TABLE 12

USP Enteric Dissolution

| | Percent Dissolution (%) | |
|---|---|---|
| | 0.1N HCl (pH ~1.2), 120 min | Phosphate (pH 6.8), 45 min |
| Lot A1 | | |
| Sample 1 | 1 | 2 |
| Sample 2 | 0 | 4 |
| Sample 3 | 1 | 3 |
| Sample 4 | 45 | 19 |
| Sample 5 | 0 | 3 |
| Sample 6 | 0 | 3 |
| Lot A4 | | |
| Sample 1 | 38 | 17 |
| Sample 2 | 47 | 6 |
| Sample 3 | 38 | 12 |
| Sample 4 | 38 | 3 |
| Sample 5 | 40 | 19 |
| Sample 6 | 36 | 5 |

What is claimed:

1. An oral enteric soft capsule shell formed from a gel mass composition comprising:
    (a) at least one or more film-forming polymers comprising a Type A or a Type B gelatin;
    (b) at least one or more acid-insoluble polymers comprising poly(methacylic acid-co-ethyl acrylate) 1:1 in an amount of about 8% to about 12% of the total gel mass;
    (c) at least one or more plasticizers;
    (d) a solvent; and
    (e) optionally an alkali neutralizing-agent
    wherein a ratio of the optional alkali neutralizing-agent to the acid-insoluble polymers is 1:14 to 1:3, and wherein a ratio of the gelatin to the acid-insoluble polymer(s) is 2.5:1 to 3:1.

2. The composition of claim 1, wherein the one or more film-forming polymers comprises about 10% to about 40% of the total gel mass.

3. The composition of claim 1, wherein the Type B gelatin comprises lime bone gelatin.

4. The composition of claim 1, wherein the Type B gelatin has a Bloom strength of about 130 grams to about 170 grams.

5. The composition of claim 1, wherein the Type B gelatin comprises about 20% to about 32% of the total gel mass.

6. The composition of claim 1, wherein the one or more acid-insoluble polymers comprises about 5% to about 20% of the total gel mass.

7. The composition of claim 1, wherein the one or more acid-insoluble polymers comprises acrylic and methacrylate acid copolymers, cellulose acetate phthalate (CAP), cellulose acetate butyrate, hydroxypropylmethylcellulose phthalate (HPMCP), sodium alginate, pectin, potassium alginate, or a combination thereof.

8. The composition of claim 1, wherein the acid-insoluble polymer further comprises one or more acrylic and methacrylate acid copolymers comprising:
poly(ethyl acrylate-co-methyl methacrylate) 2:1 or
poly(methyl acrylate-co-methyl methacrylate-co-methacrylic acid) 7:3:1 or
combinations thereof.

9. The composition of claim 8, wherein the weight ratio of poly(methacylic acid-co-ethyl acrylate) 1:1 to poly(ethyl acrylate-co-methyl methacrylate) 2:1 is about 1:1 to about 44:1.

10. The composition of claim 8, wherein the weight ratio of poly(methacylic acid-co-ethyl acrylate) 1:1 to poly(methyl acrylate-co-methyl methacrylate-co-methacrylic acid) 7:3:1 is about 1:6 to about 5:1.

11. The composition of claim 8, wherein poly(methacylic acid-co-ethyl acrylate) 1:1 comprises about 2% to about 15% of the total gel mass.

12. The composition of claim 8, wherein poly(ethyl acrylate-co-methyl methacrylate) 2:1 comprises about 0.25% to about 4% of the total gel mass.

13. The composition of claim 8, wherein poly(methyl acrylate-co-methyl methacrylate-co-methacrylic acid) 7:3:1 comprises about 1% to about 14% of the total gel mass.

14. The composition of claim 1 wherein the one or more plasticizers comprise sorbitol, non-crystallizing sorbitol, corn syrup, maltitol, glycerol, polyethylene glycol, citric acid, citric acid esters, triethyl citrate, or combinations thereof and wherein the total weight percentage of the one or more plasticizers comprises about 8% to about 30% of the total gel mass.

15. A method for preparing the enteric soft capsule according to claim 1 comprising:
(a) combining dry shell components comprising a gelatin composition and one or more acid-insoluble polymers together to form a dry mixture;
(b) adding plasticizer, solvent, and optionally an alkali neutralizing agent to the dry mixture with agitation to form a wet mixture;
(c) heating the wet mixture with agitation and applying vacuum deaeration to form a gel mass;
(d) heating the gel mass for an additional period;
(e) forming an enteric soft capsule using rotary die technology; and
(f) drying the enteric soft capsule.

16. The enteric soft capsule formed according to the method of claim 15, wherein: (a) the gelatin composition comprises a Type A gelatin having a Bloom strength of about 175 to about 195 grams or a Type B gelatin having a Bloom strength of about 150 grams;
(b) the two or more acid-insoluble polymers comprises two or more of poly(methacrylic acid-co-ethyl acrylate) 1:1, and poly (ethyl acrylate-co-methyl methacrylate) 2:1, and/or poly (methyl acrylate-co-methyl methacrylate-co-methacrylic acid) 7:3:1;
(c) the one or more plasticizers comprise glycerol;
(d) the optional alkali neutralizing agent comprises sodium hydroxide; and
(e) the solvent comprises water.

17. An oral enteric soft capsule shell formed from a gel mass composition comprising:
(a) at least one or more film-forming polymers;
(b) at least two acid-insoluble polymers comprising poly (methacylic acid-co-ethyl acrylate) 1:1 and poly(methyl acrylate-co-methyl methacrylate-co-methacrylic acid) 7:3:1;
(c) at least one or more plasticizers; and
(d) a solvent,
wherein the ratio of poly(methacylic acid-co-ethyl acrylate) 1:1 to poly(methyl acrylate-co-methyl methacrylate-co-methacrylic acid) 7:3:1 is about 1:6 to about 5:1, and wherein a ratio of the film forming polymer to the acid-insoluble polymer(s) is 2.5:1 to 3:1.

18. The composition of claim 17, wherein the two acid-insoluble polymers comprises about 5% to about 20% of the total gel mass.

19. The composition of claim 18 further comprising a non-volatile alkali neutralizing agent comprising sodium hydroxide or potassium hydroxide.

20. The composition of claim 18, wherein the total weight percentage of the non-volatile alkali neutralizing agent comprises about 1% to about 7% of the total gel mass.

21. The composition of claim 17, wherein the one or more film-forming polymers comprises Type A gelatin or Type B gelatin, wherein the Type A gelatin comprises acid bone, pig skin, poultry, fish, gelatin hydrolysate, or acid hide; and the Type B gelatin comprises lime bone gelatin.

22. The composition of claim 17, wherein the ratio of poly(methacylic acid-co-ethyl acrylate) 1:1 to poly(methyl acrylate-co-methyl methacrylate-co-methacrylic acid) 7:3:1 is about 2:1 to about 3:1.

* * * * *